United States Patent
Vu et al.

(10) Patent No.: US 7,671,238 B2
(45) Date of Patent: Mar. 2, 2010

(54) ARYLAMINO-ARYLPROPANOLAMINE DERIVATIVES AND METHODS OF THEIR USE

(75) Inventors: An Thien Vu, Pottstown, PA (US); Stephen Todd Cohn, Spring, TX (US); Eugene Anthony Terefenko, Center Valley, PA (US); William Jay Moore, Collegeville, PA (US); Puwen Zhang, Audubon, PA (US); Paige Erin Mahaney, Pottstown, PA (US); Eugene John Trybulski, Huntingdon Valley, PA (US)

(73) Assignee: Wyeth LLC, Madison, NJ (US)

(*) Notice: Subject to any disclaimer, the term of this patent is extended or adjusted under 35 U.S.C. 154(b) by 112 days.

(21) Appl. No.: 11/866,158

(22) Filed: Oct. 2, 2007

(65) Prior Publication Data

US 2008/0085938 A1  Apr. 10, 2008

Related U.S. Application Data

(60) Provisional application No. 60/849,226, filed on Oct. 4, 2006.

(51) Int. Cl.
*C07C 215/00* (2006.01)
*A01N 33/02* (2006.01)
*A61K 31/135* (2006.01)

(52) U.S. Cl. ...................... 564/355; 514/653
(58) Field of Classification Search .................. None
See application file for complete search history.

(56) References Cited

U.S. PATENT DOCUMENTS 7,517,899 B2* 4/2009 Kim et al. .................. 514/394

OTHER PUBLICATIONS

Igarashi et al. Chem. Pharm. Bull. 48 (11) 1689-1697 (2000).*
Melloni et al, European Journal of Medicinal Chemistry, 19, 235-242, 1984.

* cited by examiner

*Primary Examiner*—Daniel M Sullivan
*Assistant Examiner*—Clinton Brooks
(74) *Attorney, Agent, or Firm*—Doina G. Ene

(57) ABSTRACT

The present invention is directed to arylamino-arylpropanolamine derivatives of formula I:

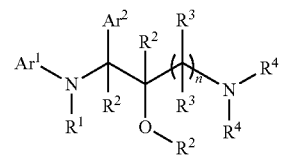

or a pharmaceutically acceptable salt thereof, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

19 Claims, 2 Drawing Sheets

ARYLAMINO-ARYLPROPANOLAMINE DERIVATIVES AND METHODS OF THEIR USE

CROSS REFERENCE TO RELATED APPLICATIONS

This application claims the benefit of U.S. Application No. 60/849,226 filed Oct. 4, 2006, the disclosure of which is incorporated herein by reference.

FIELD OF THE INVENTION

The present invention is directed to arylamino-arylpropanolamine derivatives, compositions containing these derivatives, and methods of their use for the prevention and treatment of conditions ameliorated by monoamine reuptake, including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

BACKGROUND OF THE INVENTION

Vasomotor symptoms (VMS), referred to as hot flushes and night sweats, are the most common symptoms associated with menopause, occurring in 60% to 80% of all women following natural or surgically-induced menopause. VMS are likely to be an adaptive response of the central nervous system (CNS) to declining sex steroids. To date, the most effective therapies for VMS are hormone-based treatments, including estrogens and/or some progestins. Hormonal treatments are very effective at alleviating VMS, but they are not appropriate for all women. It is well recognized that VMS are caused by fluctuations of sex steroid levels and can be disruptive and disabling in both males and females. A hot flush can last up to thirty minutes and vary in their frequency from several times a week to multiple occurrences per day. The patient experiences a hot flash as a sudden feeling of heat that spreads quickly from the face to the chest and back and then over the rest of the body. It is usually accompanied by outbreaks of profuse sweating. It may sometimes occur several times an hour, and it often occurs at night. Hot flushes and outbreaks of sweats occurring during the night can cause sleep deprivation. Psychological and emotional symptoms observed, such as nervousness, fatigue, irritability, insomnia, depression, memory loss, headache, anxiety, nervousness or inability to concentrate are considered to be caused by the sleep deprivation following hot flush and night sweats (Kramer et al., In: Murphy et al., $3^{rd}$ Int'l *Symposium on Recent Advances in Urological Cancer Diagnosis and Treatment—Proceedings*, Paris, France: SCI: 3-7 (1992)).

Hot flushes may be even more severe in women treated for breast cancer for several reasons: 1) many survivors of breast cancer are given tamoxifen, the most prevalent side effect of which is hot flush, 2) many women treated for breast cancer undergo premature menopause from chemotherapy, 3) women with a history of breast cancer have generally been denied estrogen therapy because of concerns about potential recurrence of breast cancer (Loprinzi, et al., *Lancet*, 2000, 356(9247): 2059-2063).

Men also experience hot flushes following steroid hormone (androgen) withdrawal. This is true in cases of age-associated androgen decline (Katovich, et al., *Proceedings of the Society for Experimental Biology & Medicine*, 1990, 193 (2): 129-35) as well as in extreme cases of hormone deprivation associated with treatments for prostate cancer (Berendsen, et al., *European Journal of Pharmacology*, 2001, 419(1): 47-54). As many as one-third of these patients will experience persistent and frequent symptoms severe enough to cause significant discomfort and inconvenience.

The precise mechanism of these symptoms is unknown but generally is thought to represent disturbances to normal homeostatic mechanisms controlling thermoregulation and vasomotor activity (Kronenberg et al., "Thermoregulatory Physiology of Menopausal Hot Flashes: A Review," *Can. J. Physiol. Pharmacol.*, 1987, 65:1312-1324).

The fact that estrogen treatment (e.g. estrogen replacement therapy) relieves the symptoms establishes the link between these symptoms and an estrogen deficiency. For example, the menopausal stage of life is associated with a wide range of other acute symptoms as described above and these symptoms are generally estrogen responsive.

It has been suggested that estrogens may stimulate the activity of both the norepinephrine (NE) and/or serotonin (5-HT) systems (*J. Pharmacology & Experimental Therapeutics*, 1986, 236(3) 646-652). It is hypothesized that estrogens modulate NE and 5-HT levels providing homeostasis in the thermoregulatory center of the hypothalamus. The descending pathways from the hypothalamus via brainstem/ spinal cord and the adrenals to the skin are involved in maintaining normal skin temperature. The action of NE and 5-HT reuptake inhibitors is known to impinge on both the CNS and peripheral nervous system (PNS). The pathophysiology of VMS is mediated by both central and peripheral mechanisms and, therefore, the interplay between the CNS and PNS may account for the efficacy of dual acting SRI/NRIs in the treatment of thermoregulatory dysfunction. In fact, the physiological aspects and the CNS/PNS involvement in VMS may account for the lower doses proposed to treat VMS (Loprinzi, et al., *Lancet*, 2000, 356:2059-2063; Stearns et al., *JAMA*, 2003, 289:2827-2834) compared to doses used to treat the behavioral aspects of depression. The interplay of the CNS/ PNS in the pathophysiology of VMS and the presented data within this document were used to support the claims that the norepinephrine system could be targeted to treat VMS.

Although VMS are most commonly treated by hormone therapy (orally, transdermally, or via an implant), some patients cannot tolerate estrogen treatment (Berendsen, *Maturitas*, 2000, 36(3): 155-164, Fink et al., *Nature*, 1996, 383(6598): 306). In addition, hormone replacement therapy is usually not recommended for women or men with or at risk for hormonally sensitive cancers (e.g. breast or prostate cancer). Thus, non-hormonal therapies (e.g. fluoxetine, paroxetine [SRIs] and clonidine) are being evaluated clinically. WO9944601 discloses a method for decreasing hot flushes in a human female by administering fluoxetine. Other options have been studied for the treatment of hot flashes, including steroids, alpha-adrenergic agonists, and beta-blockers, with varying degree of success (Waldinger et al., *Maturitas*, 2000, 36(3): 165-168).

It has been reported that $\alpha_2$-adrenergic receptors play a role in thermoregulatory dysfunctions (Freedman et al., *Fertility & Sterility*, 2000, 74(1): 20-3). These receptors are located both pre- and post-synaptically and mediate an inhibitory role in the central and peripheral nervous system. There are four distinct subtypes of the adrenergic $\alpha_2$ receptors, i.e., are $\alpha_{2A}$, $\alpha_{2B}$, $\alpha_{2C}$ and $\alpha_{2D}$ (Mackinnon et al., *TIPS*, 1994, 15: 119; French, *Pharmacol. Ther.*, 1995, 68: 175). It has been reported that a non-select $\alpha_2$-adrenoceptor antagonist, yohimbine, induces a flush and an $\alpha_2$-adrenergic receptor agonist, clonidine, alleviates the yohimbine effect (Katovich, et al., *Proceedings of the Society for Experimental Biology & Medicine*, 1990, 193(2): 129-35, Freedman et al., *Fertility & Sterility*, 2000, 74(1): 20-3). Clonidine has been used to treat hot flash. However, using such treatment is associated with a number of undesired side effects caused by high doses necessary to abate hot flash described herein and known in the related arts.

Chronic pain comes in many forms including visceral, inflammatory or neuropathic and crosses all therapeutic areas. It is a debilitating condition that exerts a high social cost in terms of productivity, economic impact and quality of life and current therapies have limited efficacy. Currently, first-line pharmacological treatments for neuropathic pain (i.e., diabetic neuropathy and post-herpetic neuralgia) and fibromyalgia include off-label use of the tricyclic (TCA) antidepressants (e.g., amytriptyline) and anticonvulsants (e.g., gabapentin) (Collins et al *J Pain Symptom Manage*. 2000, 20(6):449-58; and Marcus *Expert Opin Pharmacother*. 2003, 4(10): 1687-95.). However, these therapies are only effective in 30-50% of patients and produce only a partial reduction in pain (~50%). In addition, the clinical benefits of these therapies are often outweighed by the side effects including: dry mouth and sedation. Therefore, newer classes of compounds including non-TCA antidepressants are being evaluated preclinically and clinically for chronic pain indications and recently duloxetine was approved for the treatment of diabetic neuropathy. Although more tolerable than the older tricyclic antidepressants these newer compounds are not devoid of side effects that include, sexual dysfunction, weight gain and nausea.

While the precise pathophysiological mechanisms involved in the development and maintenance of chronic pain states are not fully understood, the pathways involved in pain perception and modulation have been well described and characterized (Gebhart, In: Yaksh TL, editor. Spinal afferent processing, New York: Plenum, 1986. pp 391-416; Fields, et al. *Annual Review of Neuroscience* 1991, 14: 219-245; Fields, et al. In: Wall PD, Melzack R, editors. Textbook of pain, London: Churchill Livingstone, 1999, pp 309-329; Millan, et al. *Progress in Neurobiology*, 2002, 66:355-474). A major component of this descending pain inhibitory system involves the noradrenergic pathway (Zhuo, et al. *Brain Research* 1991; 550:35-48; Holden, et al. *Neuroscience* 1999; 91: 979-990). It is assumed that norepinephrine (NE) and to a lesser extent serotonin (5-HT) reuptake inhibitors NRIs and SRIs, attenuate pain by preventing presynaptic reuptake of NE/5-HT leading to increased postsynaptic NE/5-HT levels and sustained activation of this descending pain inhibitory pathway. A meta-analysis of antidepressants and neuropathic pain comparing the efficacy of known NRIs, mixed NRI/SRIs and SRIs determined that compounds with NRI activity were more effective in reducing pain, and that select SRIs did not significantly differ from placebo (Collins et al. *J Pain Symptom Manage*. 2000, 20(6): 449-58). This analysis suggests that compounds with greater NRI versus SRI activity will be more effective for the treatment of pain.

Published U.S. Applications US 2005-0222148 A1 and US 2005-0222142 A1 disclose derivatives of phenylaminopropanol, compositions containing these derivatives, and methods of their use for the prevention and treatment of conditions ameliorated by monoamine reuptake.

Given the complex multifaceted nature of thermoregulation and the interplay between the CNS and PNS in maintaining thermoregulatory homeostasis, multiple therapies and approaches can be developed to target vasomotor symptoms.

The present invention focuses on novel compounds and compositions containing these compounds directed to these and other important uses.

SUMMARY OF THE INVENTION

The present invention is directed to arylamino-arylpropanolamine derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

In one embodiment, the present invention is directed to compounds of formula I:

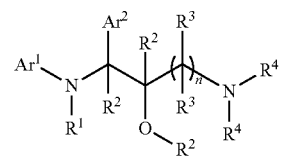

or a pharmaceutically acceptable salt thereof;
wherein:
n is 1 or 2;
$Ar^1$ is phenyl or naphthyl, wherein said phenyl or naphthyl is optionally substituted with up to 4 groups $R^5$;
$Ar^2$ is phenyl or naphthyl, wherein said phenyl or naphthyl is optionally substituted with up to 4 groups $R^5$;
$R^1$ is hydrogen or $C_1$-$C_3$ alkyl;
each $R^2$ is, independently, hydrogen or $C_1$-$C_3$ alkyl;
each $R^3$ is, independently, hydrogen or $C_1$-$C_3$ alkyl;
each $R^4$ is, independently, hydrogen or $C_1$-$C_4$ alkyl;
each $R^5$ is, independently, $C_1$-$C_3$ alkyl, $C_1$-$C_3$ alkoxy, halo, $CF_3$, $OCF_3$, hydroxy, nitro, nitrile, $C_2$-$C_4$ alkenyl, or $C_2$-$C_5$ alkynyl;
provided that said compound of formula I is other than 1-[(2-methoxyphenyl) (methyl)amino]-3-(methylamino)-1-phenylpropan-2-ol.

In yet other embodiments, the present invention is directed to compositions, comprising:
a. at least one compound of formula I; and
b. at least one pharmaceutically acceptable carrier.

In another embodiment, the present invention is directed to methods for treating or preventing a condition ameliorated by monoamine reuptake in a subject in need thereof, comprising the step of:
administering to said subject an effective amount of a compound of formula I or pharmaceutically acceptable salt thereof. The conditions ameliorated by monoamine reuptake include those selected from the group consisting of vasomotor symptoms, sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

In another embodiment, the present invention is directed to methods for treating or preventing vasomotor symptoms in a subject in need thereof, comprising the step of:

administering to said subject an effective amount of at least one compound of formula I or pharmaceutically acceptable salt thereof.

In yet another embodiment, the present invention is directed to methods for treating or preventing a depression disorder in a subject in need thereof, comprising the step of:

administering to said subject an effective amount of at least one compound of formula I or pharmaceutically acceptable salt thereof.

In yet other embodiments, the present invention is directed to methods for treating or preventing sexual dysfunction in a subject in need thereof, comprising the step of:

administering to said subject an effective amount of at least one compound of formula I or pharmaceutically acceptable salt thereof.

In further embodiments, the present invention is directed to methods for treating or preventing pain in a subject in need thereof, comprising the step of:

administering to said subject an effective amount of at least one compound of formula I or pharmaceutically acceptable salt thereof.

In another embodiment, the present invention is directed to methods for treating or preventing gastrointestinal or genitourinary disorder, particularly stress incontinence or urge urinary incontinence, in a subject in need thereof, comprising the step of:

administering to said subject an effective amount of a compound of formula I or pharmaceutically acceptable salt thereof.

In another embodiment, the present invention is directed to methods for treating or preventing chronic fatigue syndrome in a subject in need thereof, comprising the step of:

administering to said subject an effective amount of a compound of formula I or pharmaceutically acceptable salt thereof.

In another embodiment, the present invention is directed to methods for treating or preventing fibromyalgia syndrome in a subject in need thereof, comprising the step of:

administering to said subject an effective amount of a compound of formula I or pharmaceutically acceptable salt thereof.

BRIEF DESCRIPTION OF THE DRAWINGS

The invention can be more fully understood from the following detailed description and the accompanying drawings that form a part of this application.

DETAILED DESCRIPTION OF THE INVENTION

Figure 1:
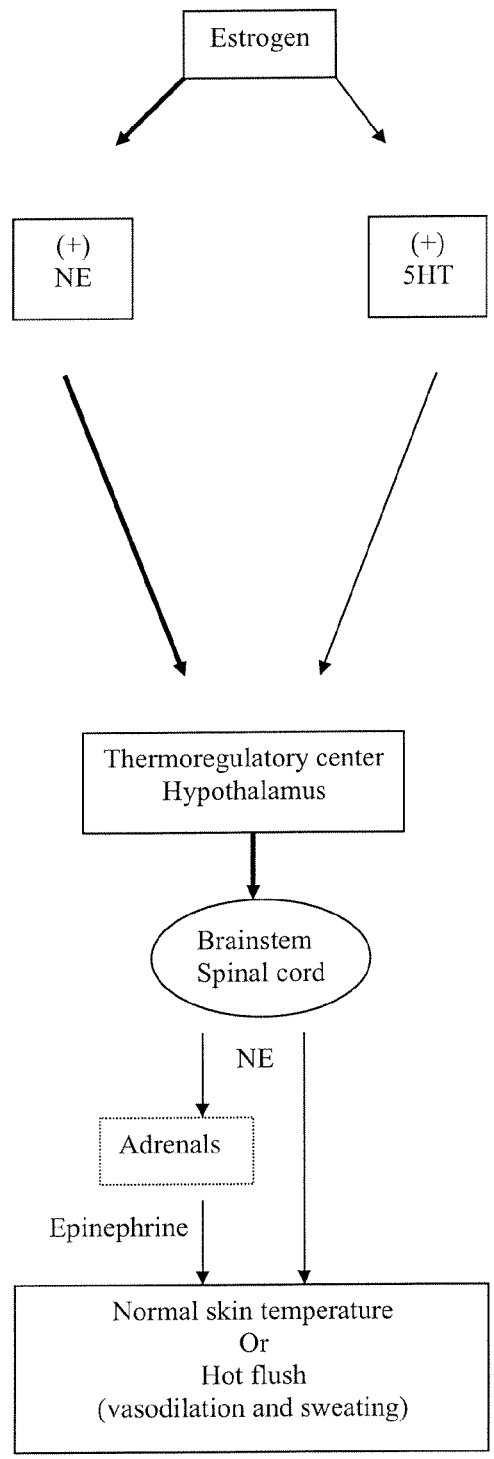
FIG. 1 is an overview of estrogen action on norepinephrine/serotonin mediated thermoregulation.

The present invention is directed to arylamino-arylpropanolamine derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

The following definitions are provided for the full understanding of terms and abbreviations used in this specification.

As used herein and in the appended claims, the singular forms "a," "an," and "the" include the plural reference unless the context clearly indicates otherwise. Thus, for example, a reference to "an antagonist" includes a plurality of such antagonists, and a reference to "a compound" is a reference to one or more compounds and equivalents thereof known to those skilled in the art, and so forth.

The abbreviations in the specification correspond to units of measure, techniques, properties, or compounds as follows: "min" means minutes, "h" means hour(s), "µL" means microliter(s), "mL" means milliliter(s), "mM" means millimolar, "M" means molar, "mmole" means millimole(s), "cm" means centimeters, "SEM" means standard error of the mean and "IU" means International Units. "Δ° C." and Δ "ED$_{50}$ value" means dose which results in 50% alleviation of the observed condition or effect (50% mean maximum endpoint).

"Norepinephrine transporter" is abbreviated NET.

"Human norepinephrine transporter" is abbreviated hNET.

"Serotonin transporter" is abbreviated SERT.

"Human serotonin transporter" is abbreviated hSERT.

"Norepinephrine reuptake inhibitor" is abbreviated NRI.

"Selective norepinephrine reuptake inhibitor" is abbreviated SNRI.

"Serotonin reuptake inhibitor" is abbreviated SRI.

"Selective serotonin reuptake inhibitor" is abbreviated SSRI.

"Norepinephrine" is abbreviated NE.

"Serotonin" is abbreviated 5-HT.

"Subcutaneous" is abbreviated sc.

"Intraperitoneal" is abbreviated ip.

"Oral" is abbreviated po.

In the context of this disclosure, a number of terms shall be utilized. The term "treatment" as used herein includes preventative (e.g., prophylactic), curative or palliative treatment and "treating" as used herein also includes preventative, curative and palliative treatment.

The term "effective amount," as used herein, refers to an amount effective, at dosages, and for periods of time necessary, to achieve the desired result with respect to prevention or treatment of vasomotor symptoms, depression disorders, sexual dysfunction, or pain. In particular, with respect to vasomotor symptoms, "effective amount" refers to the amount of compound or composition of compounds that would increase norepinephrine levels to compensate in part or total for the lack of steroid availability in subjects subject afflicted with a vasomotor symptom. Varying hormone levels will influence the amount of compound required in the present invention. For example, the pre-menopausal state may require a lower level of compound due to higher hormone levels than the peri-menopausal state.

It will be appreciated that the effective amount of components of the present invention will vary from patient to patient not only with the particular compound, component or composition selected, the route of administration, and the ability of the components (alone or in combination with one or more combination drugs) to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects.

Preferably, the compounds of the present invention are administered at a dosage and for a time such that the number of hot flushes is reduced as compared to the number of hot flushes prior to the start of treatment. Such treatment can also be beneficial to reduce the overall severity or intensity distribution of any hot flushes still experienced, as compared to the severity of hot flushes prior to the start of the treatment. With respect to depression disorders, sexual dysfunction, and pain, the compounds of the present invention are administered at a dosage and for a time such that there is the prevention, alleviation, or elimination of the symptom or condition.

For example, for an afflicted patient, compounds of formula I, or a pharmaceutically acceptable salt thereof, may be administered, preferably, at a dosage of from about 0.1 mg/day to about 500 mg/day, dosed one or two times daily, more preferably from about 1 mg/day to about 200 mg/day and most preferably from about 1 mg/day to 100 mg/day for a time sufficient to reduce and/or substantially eliminate the number and/or severity of hot flushes or symptom or condition of the depression disorder, sexual dysfunction, or pain.

The terms "component," "composition of compounds," "compound," "drug," or "pharmacologically active agent" or "active agent" or "medicament" are used interchangeably herein to refer to a compound or compounds or composition of matter which, when administered to a subject (human or animal) induces a desired pharmacological and/or physiologic effect by local and/or systemic action.

The terms "component", "drug" or "pharmacologically active agent" or "active agent" or "medicament" are used interchangeably herein to refer to a compound or compounds or composition of matter which, when administered to an organism (human or animal) induces a desired pharmacologic and/or physiologic effect by local and/or systemic action.

The term "modulation" refers to the capacity to either enhance or inhibit a functional property of a biological activity or process, for example, receptor binding or signaling activity. Such enhancement or inhibition may be contingent on the occurrence of a specific event, such as activation of a signal transduction pathway and/or may be manifest only in particular cell types. The modulator is intended to comprise any compound, e.g., antibody, small molecule, peptide, oligopeptide, polypeptide, or protein, preferably small molecule, or peptide.

As used herein, the term "inhibitor" refers to any agent that inhibits, suppresses, represses, or decreases a specific activity, such as serotonin reuptake activity or the norepinephrine reuptake activity. The term "inhibitor" is intended to comprise any compound, e.g., antibody, small molecule, peptide, oligopeptide, polypeptide, or protein, preferably small molecule or peptide, that exhibits a partial, complete, competitive and/or inhibitory effect on mammalian, preferably the human norepinephrine reuptake or both serotonin reuptake and the norepinephrine reuptake, thus diminishing or blocking, preferably diminishing, some or all of the biological effects of endogenous norepinephrine reuptake or of both serotonin reuptake and the norepinephrine reuptake.

Within the present invention, the compounds of formula I may be prepared in the form of pharmaceutically acceptable salts. As used herein, the term "pharmaceutically acceptable salts" refers to salts prepared from pharmaceutically acceptable non-toxic acids, including inorganic salts, and organic salts. Suitable non-organic salts include inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and the like. Particularly preferred are hydrochloric, hydrobromic, phosphoric, and sulfuric acids, and most preferably is the hydrochloride salt.

"Administering," as used herein, means either directly administering a compound or composition of the present invention, or administering a prodrug, derivative or analog which will form an equivalent amount of the active compound or substance within the body.

The term "subject" or "patient" refers to an animal including the human species that is treatable with the compositions, and/or methods of the present invention. The term "subject" or "subjects" is intended to refer to both the male and female gender unless one gender is specifically indicated. Accordingly, the term "patient" comprises any mammal which may benefit from treatment or prevention of vasomotor symptoms, depression disorders, sexual dysfunction, or pain, such as a human, especially if the mammal is female, either in the pre-menopausal, peri-menopausal, or post-menopausal period. Furthermore, the term patient includes female animals including humans and, among humans, not only women of advanced age who have passed through menopause but also women who have undergone hysterectomy or for some other reason have suppressed estrogen production, such as those who have undergone long-term administration of corticosteroids, suffer from Cushing's syndrome or have gonadal dysgenesis. However, the term "patient" is not intended to be limited to a woman.

The terms "premature menopause" or "artificial menopause" refer to ovarian failure of unknown cause that may occur before age 40. It may be associated with smoking, living at high altitude, or poor nutritional status. Artificial menopause may result from oophorectomy, chemotherapy, radiation of the pelvis, or any process that impairs ovarian blood supply.

The term "pre-menopausal" means before the menopause, the term "peri-menopausal" means during the menopause, and the term "post-menopausal" means after the menopause. "Ovariectomy" means removal of an ovary or ovaries and can be effected according to Merchenthaler et al., *Maturitas*, 1998, 30(3): 307-316.

"Side effect" refers to a consequence other than the one(s) for which an agent or measure is used, as the adverse effects produced by a drug, especially on a tissue or organ system other then the one sought to be benefited by its administration. In the case, for example, of high doses of NRIs or NRI/SRI compounds alone, the term "side effect" may refer to such conditions as, for example, vomiting, nausea, sweating, and flushes (Janowsky, et al., *Journal of Clinical Psychiatry*, 1984, 45(10 Pt 2): 3-9).

"Vasomotor symptoms," "vasomotor instability symptoms" and "vasomotor disturbances" include, but are not limited to, hot flushes (flashes), insomnia, sleep disturbances, mood disorders, irritability, excessive perspiration, night sweats, fatigue, and the like, caused by, inter alia, thermoregulatory dysfunction.

The term "hot flush" is an art-recognized term that refers to an episodic disturbance in body temperature typically consisting of a sudden skin flushing, usually accompanied by perspiration in a subject.

The term "sexual dysfunction" includes, but is not limited to, condition relating to desire and/or arousal.

As used herein, "gastrointestinal and genitourinary disorders" includes irritable bowel syndrome, symptomatic GERD, hypersensitive esophagus, nonulcer dyspepsia, non-cardiac chest pain, biliary dyskinesia, sphincter of Oddi dysfunction, incontinence (i.e., urge incontinence, stress incontinence, genuine stress incontinence, and mixed incontinence)(including the involuntary voiding of feces or urine, and dribbling or leakage or feces or urine which may be due to one or more causes including but not limited to pathology altering sphincter control, loss of cognitive function, overdistention of the bladder, hyperreflexia and/or involuntary urethral relaxation, weakness of the muscles associated with the bladder or neurologic abnormalities), interstitial cystitis (irritable bladder), and chronic pelvic pain (including, but not limited to vulvodynia, prostatodynia, and proctalgia).

As used herein, "chronic fatigue syndrome" (CFS) is a condition characterized by physiological symptoms selected from weakness, muscle aches and pains, excessive sleep, malaise, fever, sore throat, tender lymph nodes, impaired memory and/or mental concentration, insomnia, disordered sleep, localized tenderness, diffuse pain and fatigue, and combinations thereof.

As used herein, "fibromyalgia syndrome" (FMS) includes FMS and other somatoform disorders, including FMS associated with depression, somatization disorder, conversion disorder, pain disorder, hypochondriasis, body dysmorphic disorder, undifferentiated somatoform disorder, and somatoform NOS. FMS and other somatoform disorders are accompanied by physiological symptoms selected from a generalized heightened perception of sensory stimuli, abnormalities in pain perception in the form of allodynia (pain with innocuous stimulation), abnormalities in pain perception in the form of hyperalgesia (increased sensitivity to painful stimuli), and combinations thereof.

As used herein, "nervous system disorders," includes addictive disorders (including those due to alcohol, nicotine, and other psychoactive substances) and withdrawal syndrome, age-associated learning and mental disorders (including Alzheimer's disease), anorexia nervosa, bulimia nervosa, attention-deficit disorder with or without hyperactivity disorder bipolar disorder, pain, cyclothymic disorder, depression disorder (including major depressive disorder, refractory depression adolescent depression and minor depression), dysthymic disorder, generalized anxiety disorder (GAD), obesity (i.e., reducing the weight of obese or overweight patients), obsessive compulsive disorders and related spectrum disorders, oppositional defiant disorder, panic disorder, post-traumatic stress disorder, premenstrual dysphoric disorder (i.e., premenstrual syndrome and late luteal phase dysphoric disorder), psychotic disorders (including schizophrenia, schizoaffective and schizophreniform disorders), seasonal affective disorder, sleep disorders (such as narcolepsy and enuresis), social phobia (including social anxiety disorder), selective serotonin reuptake inhibition (SSRI) "poop out" syndrome (i.e., wherein a patient who fails to maintain a satisfactory response to SSRI therapy after an initial period of satisfactory response).

As used herein, "pain," includes both acute pain and chronic pain, which may be centralized pain, peripheral pain, or combination thereof. The term includes many different types of pains including, but not limited to, neuropathic pain, visceral pain, musculoskeletal pain, bony pain, cancer pain, inflammatory pain, and combinations thereof, such as lower back pain, atypical chest pain, headache such as cluster headache, migraine, herpes neuralgia, phantom limb pain, pelvic pain, myofascial face pain, abdominal pain, neck pain, central pain, dental pain, opioid resistant pain, visceral pain, surgical pain, bone injury pain, pain during labor and delivery, pain resulting from burns, post partum pain, angina pain, neuropathic pain such as peripheral neuropathy and diabetic neuropathy, post-operative pain, and pain which is co-morbid with nervous system disorders described herein.

As used herein, the term "acute pain" refers to centralized or peripheral pain that is intense, localized, sharp, or stinging, and/or dull, aching, diffuse, or burning in nature and that occurs for short periods of time.

As used herein, the term "chronic pain" refers to centralized or peripheral pain that is intense, localized, sharp, or stinging, and/or dull, aching, diffuse, or burning in nature and that occurs for extended periods of time (i.e., persistent and/or regularly reoccurring), including, for the purpose of the present invention, neuropathic pain and cancer pain. Chronic pain includes neuropathic pain, hyperalgesia, and/or allodynia.

As used herein, the term "neuropathic pain" refers to chronic pain caused by damage to or pathological changes in the peripheral or central nervous systems. Examples of pathological changes related to neuropathic pain include prolonged peripheral or central neuronal sensitization, central sensitization related damage to nervous system inhibitory and/or exhibitory functions and abnormal interactions between the parasympathetic and sympathetic nervous systems. A wide range of clinical conditions may be associated with or form the basis for neuropathic pain including, for example, diabetes, post traumatic pain of amputation (nerve damage cause by injury resulting in peripheral and/or central sensitization such as phantom limb pain), lower back pain, cancer, chemical injury, toxins, other major surgeries, peripheral nerve damage due to traumatic injury compression, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, reflex sympathetic dystrophy or post thoracotomy pain, nutritional deficiencies, or viral or bacterial infections such as shingles or human immunodeficiency virus (HIV), and combinations thereof. Also included in the definition of neuropathic pain is a condition secondary to metastatic infiltration, adiposis dolorosa, burns, central pain conditions related to thalamic conditions, and combinations thereof.

As used herein, the term "hyperalgesia" refers to pain where there is an increase in sensitivity to a typically noxious stimulus.

As used herein, the term "allodynia" refers to an increase in sensitivity to a typically non-noxious stimulus.

As used herein, the term "visceral pain" refers to pain associated with or resulting from maladies of the internal organs, such as, for example, ulcerative colitis, irritable bowel syndrome, irritable bladder, Crohn's disease, rheumatologic (arthralgias), tumors, gastritis, pancreatitis, infections of the organs, biliary tract disorders, and combinations thereof.

As used herein, the term "female-specific pain" refers to pain that may be acute and/or chronic pain associated with female conditions. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes, and combinations thereof.

"Alkyl," as used herein, refers to an optionally substituted, saturated straight, branched, or cyclic hydrocarbon having from about 1 to about 20 carbon atoms (and all combinations and subcombinations of ranges and specific numbers of carbon atoms therein), with from about 1 to about 8 carbon atoms being preferred, and with from about 1 to about 4 carbon atoms, herein referred to as "lower alkyl", being more preferred. Alkyl groups include, but are not limited to, methyl, ethyl, n-propyl, isopropyl, n-butyl, isobutyl, t-butyl, n-pentyl, cyclopentyl, isopentyl, neopentyl, n-hexyl, isohexyl, cyclohexyl, cyclooctyl, adamantyl, 3-methylpentyl, 2,2-dimethylbutyl, and 2,3-dimethylbutyl.

"Alkenyl," as used herein, refers to an alkyl group of at least two carbon atoms having one or more double bonds, wherein alkyl is as defined herein. Alkenyl groups can be optionally substituted.

"Alkynyl," as used herein, refers to an alkyl group of at least two carbon atoms having one or more triple bonds, wherein alkyl is as defined herein. Alkynyl groups can be optionally substituted.

"Alkoxy," as used herein, refers to the group R—O—where R is an alkyl group as defined herein.

"Halo," as used herein, refers to chloro, bromo, fluoro, and iodo.

In one embodiment, the present invention is directed to compounds of formula I:

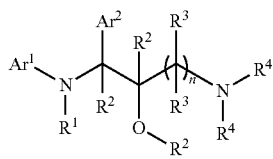

I or a pharmaceutically acceptable salt thereof;
wherein:
n is 1 or 2;
$Ar^1$ is phenyl or naphthyl, wherein said phenyl or naphthyl is optionally substituted with up to 4 groups $R^5$;
$Ar^2$ is phenyl or naphthyl, wherein said phenyl or naphthyl is optionally substituted with up to 4 groups $R^5$;
$R^1$ is hydrogen or $C_1$-$C_3$ alkyl;
each $R^2$ is, independently, hydrogen or $C_1$-$C_3$ alkyl;
each $R^3$ is, independently, hydrogen or $C_1$-$C_3$ alkyl;
each $R^4$ is, independently, hydrogen or $C_1$-$C_4$ alkyl;
each $R^5$ is, independently, $C_1$-$C_3$ alkyl, $C_1$-$C_3$ alkoxy, halo, $CF_3$, $OCF_3$, hydroxy, nitro, nitrile, $C_2$-$C_4$ alkenyl, or $C_2$-$C_5$ alkynyl;
provided that said compound of formula I is other than 1-[(2-methoxyphenyl) (methyl)amino]-3-(methylamino)-1-phenylpropan-2-ol.

In certain preferred embodiments of the compounds of formula I, n is 1. In other preferred embodiment, n is 2.

In certain preferred embodiments of the compounds of formula I, $Ar^1$ is phenyl or naphthyl, wherein said phenyl or naphthyl is substituted with no $R^5$. In certain other preferred embodiments of the compounds of formula I, $Ar^1$ is phenyl substituted with one $R^5$. In certain other preferred embodiments of the compounds of formula I, $Ar^1$ is phenyl substituted with two $R^5$. In certain other preferred embodiments of the compounds of formula I, $Ar^1$ is phenyl substituted with three $R^5$. In certain other preferred embodiments of the compounds of formula I, $Ar^1$ is phenyl substituted with four $R^5$.

In certain preferred embodiments of the compounds of formula I, $Ar^2$ is phenyl or naphthyl, wherein said phenyl or naphthyl is substituted with 0 $R^5$. In certain more preferred embodiments of the compounds of formula I, $Ar^2$ is phenyl substituted with one $R^5$. In certain more preferred embodiments of the compounds of formula I, $Ar^2$ is phenyl substituted with two $R^5$. In certain other preferred embodiments of the compounds of formula I, $Ar^2$ is phenyl substituted with three $R^5$. In certain other preferred embodiments of the compounds of formula I, $Ar^2$ is phenyl substituted with four $R^5$.

In certain preferred embodiments of the compounds of formula I, $R^1$ is hydrogen or methyl. In certain more preferred embodiments of the compounds of formula I, $R^1$ is methyl. In certain preferred embodiments of the compounds of formula I, $R^1$ is ethyl. In certain preferred embodiments of the compounds of formula I, $R^1$ is propyl.

In certain preferred embodiments of the compounds of formula I, at least one $R^2$ is hydrogen. In certain preferred embodiments of the compounds of formula I, each $R^2$ is hydrogen. In certain preferred embodiments of the compounds of formula I, $R^2$ is methyl. In certain preferred embodiments of the compounds of formula I, $R^2$ is ethyl. In certain preferred embodiments of the compounds of formula I, $R^2$ is propyl.

In certain preferred embodiments of the compounds of formula I, at least one $R^3$ is hydrogen. In certain preferred embodiments of the compounds of formula I, each $R^3$ is hydrogen. In certain preferred embodiments of the compounds of formula I, $R^3$ is methyl. In certain preferred embodiments of the compounds of formula I, $R^3$ is ethyl. In certain preferred embodiments of the compounds of formula I, $R^3$ is propyl.

In certain preferred embodiments of the compounds of formula I, each group $R^4$ is, independently, hydrogen, methyl, or ethyl. In certain more preferred embodiments of the compounds of formula I, at least one $R^4$ is hydrogen. In certain even more preferred embodiments of the compounds of formula I, each $R^4$ is hydrogen. More specifically, one group $R^4$ may be hydrogen and the other group $R^4$ may be methyl or ethyl. Alternatively, both groups $R^4$ may be methyl or ethyl. Thus, the group —$NR^5R^5$ may for example be —$NH_2$, —$NHCH_3$, —$NHC_2H_5$, —$NCH_3C_2H_5$, —$N(CH_3)_2$ or —$N(C_2H_5)_2$.

In certain preferred embodiments of the compounds of formula I, $R^5$ is, independently at each occurrence, methyl, methoxy, chloro, fluoro, $CF_3$, $OCF_3$, hydroxy, nitro, or nitrile. In certain more preferred embodiments of the compounds of formula I, $R^5$ is methyl, methoxy, chloro, or fluoro.

Preferred compounds of formula I include:
3-amino-1-[methyl(phenyl)amino]-1-phenylpropan-2-ol;
3-amino-1-[methyl(3-methylphenyl)amino]-1-phenylpropan-2-ol;
3-amino-1-[(2-chlorophenyl)(methyl)amino]-1-phenylpropan-2-ol;
3-amino-1-[(3-methoxyphenyl)(methyl)amino]-1-phenylpropan-2-ol;
3-amino-1-(4-methoxyphenyl)-1-[methyl(phenyl)amino]propan-2-ol;
3-amino-1-[(4-chlorophenyl)(methyl)amino]-1-(4-methoxyphenyl)propan-2-ol;
3-amino-1-(3-fluorophenyl)-1-[methyl(phenyl)amino]propan-2-ol;
3-(methylamino)-1-[methyl(phenyl)amino]-1-phenylpropan-2-ol;
3-(methylamino)-1-[methyl(phenyl)amino]-1-phenylpropan-2-ol;
3-(methylamino)-1-[methyl(2-methylphenyl)amino]-1-phenylpropan-2-ol;
3-(methylamino)-1-[methyl(3-methylphenyl)amino]-1-phenylpropan-2-ol;

3-(methylamino)-1-[methyl(4-methylphenyl)amino]-1-phenylpropan-2-ol;
1-[(2-chlorophenyl)(methyl)amino]-3-(methylamino)-1-phenylpropan-2-ol;
1-[(3-chlorophenyl)(methyl)amino]-3-(methylamino)-1-phenylpropan-2-ol;
1-[(4-fluorophenyl)(methyl)amino]-3-(methylamino)-1-phenylpropan-2-ol;
1-[(4-chlorophenyl)(methyl)amino]-3-(methylamino)-1-phenylpropan-2-ol;
1-[(3-methoxyphenyl)(methyl)amino]-3-(methylamino)-1-phenylpropan-2-ol;
1-[(4-methoxyphenyl)(methyl)amino]-3-(methylamino)-1-phenylpropan-2-ol;
1-(3-fluorophenyl)-3-(methylamino)-1-[methyl(phenyl)amino]propan-2-ol;
1-(3-chlorophenyl)-3-(methylamino)-1-[methyl(phenyl)amino]propan-2-ol;
1-(4-chlorophenyl)-3-(methylamino)-1-[methyl(phenyl)amino]propan-2-ol;
1-(4-methoxyphenyl)-3-(methylamino)-1-[methyl(phenyl)amino]propan-2-ol;
1-[(4-chlorophenyl)(methyl)amino]-1-(3-fluorophenyl)-3-(methylamino)propan-2-ol;
1-[(3-fluorophenyl)(methyl)amino]-1-(4-methoxyphenyl)-3-(methylamino) propan-2-ol;
1-[(4-chlorophenyl)(methyl)amino]-1-(4-methoxyphenyl)-3-(methylamino) propan-2-ol;
1-(4-methoxyphenyl)-1-[(4-methoxyphenyl)(methyl)amino]-3-(methylamino) propan-2-ol;
3-(methylamino)-1-[methyl(1-naphthyl)amino]-1-phenylpropan-2-ol;
3-(ethylamino)-1-[methyl (4-methylphenyl)amino]-1-phenylpropan-2-ol;
1-[(4-chlorophenyl)(methyl)amino]-3-(ethylamino)-1-(4-methoxyphenyl)propan-2-ol;
1-(3-chlorophenyl)-3-(ethylamino)-1-[methyl(phenyl)amino]propan-2-ol;
1-(4-chlorophenyl)-3-(ethylamino)-1-[methyl(phenyl)amino]propan-2-ol;
3-(dimethylamino)-1-[methyl(4-methylphenyl)amino]-1-phenylpropan-2-ol; and
pharmaceutically acceptable salts thereof, particularly the hydrochloride salt thereof.

Particularly preferred compounds of formula I include:
(1RS,2SR)-3-amino-1-[methyl(phenyl)amino]-1-phenylpropan-2-ol;
(1RS,2SR)-3-amino-1-[methyl(3-methylphenyl)amino]-1-phenylpropan-2-ol;
(1RS,2SR)-3-amino-1-[(2-chlorophenyl)(methyl)amino]-1-phenylpropan-2-ol;
(1RS,2SR)-3-amino-1-[(3-methoxyphenyl)(methyl)amino]-1-phenylpropan-2-ol;
(1RS,2SR)-3-amino-1-(4-methoxyphenyl)-1-[methyl(phenyl)amino]propan-2-ol;
(1RS,2SR)-3-amino-1-[(4-chlorophenyl)(methyl)amino]-1-(4-methoxyphenyl) propan-2-ol;
(1RS,2SR)-3-amino-1-(3-fluorophenyl)-1-[methyl (phenyl)amino]propan-2-ol;
(1RS,2SR)-3-(methylamino)-1-[methyl(phenyl)amino]-1-phenylpropan-2-ol;
(1RS,2RS)-3-(methylamino)-1-[methyl(phenyl)amino]-1-phenylpropan-2-ol;
(1RS,2SR)-3-(methylamino)-1-[methyl (2-methyl phenyl)amino]-1-phenylpropan-2-ol;
(1RS,2SR)-3-(methylamino)-1-[methyl (3-methyl phenyl)amino]-1-phenylpropan-2-ol;
(1RS,2SR)-3-(methylamino)-1-[methyl (4-methyl phenyl)amino]-1-phenylpropan-2-ol;
(1RS,2SR)-1-[(2-chlorophenyl)(methyl)amino]-3-(methylamino)-1-phenylpropan-2-ol;
(1RS,2SR)-1-[(3-chlorophenyl)(methyl)amino]-3-(methylamino)-1-phenylpropan-2-ol;
(1RS,2SR)-1-[(4-fluorophenyl)(methyl)amino]-3-(methylamino)-1-phenylpropan-2-ol;
(1RS,2SR)-1-[(4-chlorophenyl)(methyl)amino]-3-(methylamino)-1-phenylpropan-2-ol;
(1RS,2SR)-1-[(3-methoxyphenyl)(methyl)amino]-3-(methylamino)-1-phenylpropan-2-ol;
(1RS,2SR)-1-[(4-methoxyphenyl)(methyl)amino]-3-(methylamino)-1-phenylpropan-2-ol;
(1RS,2SR)-1-(3-fluorophenyl)-3-(methylamino)-1-[methyl (phenyl )amino] propan-2-ol;
(1RS,2SR)-1-(3-chlorophenyl)-3-(methylamino)-1-[methyl (phenyl)amino] propan-2-ol;
(1RS,2SR)-1-(4-chlorophenyl)-3-(methylamino)-1-[methyl (phenyl)amino] propan-2-ol;
(1RS,2SR)-1-(4-methoxyphenyl)-3-(methylamino)-1-[methyl(phenyl)amino] propan-2-ol;
(1RS,2SR)-1-[(4-chlorophenyl)(methyl)amino]-1-(3-fluorophenyl)-3-(methylamino)propan-2-ol;
(1RS,2SR)-1-[(3-fluorophenyl)(methyl)amino]-1-(4-methoxyphenyl)-3-(methylamino)propan-2-ol;
(1RS,2SR)-1-[(4-chlorophenyl)(methyl)amino]-1-(4-methoxyphenyl)-3-(methylamino)propan-2-ol;
(1RS,2SR)-1-(4-methoxyphenyl)-1-[(4-methoxyphenyl)(methyl)amino]-3-(methylamino)propan-2-ol;
(1RS,2SR)-3-(methylamino)-1-[methyl(1-naphthyl)amino]-1-phenylpropan-2-ol;
(1RS,2SR)-3-(ethylamino)-1-[methyl (4-methyl phenyl) amino]-1-phenylpropan-2-ol;
(1RS,2SR)-1-[(4-chlorophenyl)(methyl)amino]-3-(ethylamino)-1-(4-methoxyphenyl)propan-2-ol;
(1RS,2SR)-1-(3-chlorophenyl)-3-(ethylamino)-1-[methyl (phenyl)amino] propan-2-ol;
(1RS,2SR)-1-(4-chlorophenyl)-3-(ethylamino)-1-[methyl (phenyl)amino] propan-2-ol;
(1RS,2SR)-3-(dimethylamino)-1-[methyl (4-methyl phenyl) amino]-1-phenylpropan-2-ol; and
stereoisomers thereof and pharmaceutically acceptable salts thereof, particularly the hydrochloride salt thereof.

Some of the compounds of the present invention may contain chiral centers and such compounds may exist in the form of stereoisomers (i.e. enantiomers). The present invention includes all such stereoisomers and any mixtures thereof including racemic mixtures. Racemic mixtures of the stereoisomers as well as the substantially pure stereoisomers are within the scope of the invention. The term "substantially pure," as used herein, refers to at least about 90 mole %, more preferably at least about 95 mole %, and most preferably at least about 98 mole % of the desired stereoisomer is present relative to other possible stereoisomers. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron*, 33:2725 (1977); Eliel, E. L. *Stereochemistry of Carbon Compounds*, (McGraw-Hill, N.Y., 1962); Wilen, S. H. *Tables of Resolving Agents and Optical Resolutions*, p. 268 (E. L. Eliel, Ed., University of Notre Dame Press, Notre Dame, Ind. 1972).

The present invention includes prodrugs of the compounds of formula I. "Prodrug," as used herein, means a compound which is convertible in vivo by metabolic means (e.g. by hydrolysis) to a compound of formula I. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). "Design and Application of Prodrugs," *Textbook of Drug Design and Development*, Chapter 5, 113-191 (1991), Bundgaard, et al., *Journal of Drug Deliver Reviews*, 1992, 8:1-38, Bundgaard, J. *of Pharmaceutical Sciences*, 1988, 77:285 et seq.; and Higuchi and Stella (eds.) *Prodrugs as Novel Drug Delivery Systems*, American Chemical Society (1975).

Further, the compounds of formula I may exist in unsolvated as well as in solvated forms with pharmaceutically acceptable solvents such as water, ethanol, and the like. In general, the solvated forms are considered equivalent to the unsolvated forms for the purpose of the present invention.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991.

Compounds of the present invention are suitably prepared in accordance with the following general description and specific examples. Variables used are as defined for formula I, unless otherwise noted. The reagents used in the preparation of the compounds of this invention can be either commercially obtained or can be prepared by standard procedures described in the literature. In accordance with this invention, compounds of formula I are produced by the following reaction schemes (Scheme 1 and 2).

The compounds of this invention contain chiral centers, providing for various stereoisomeric forms such as diastereomeric mixtures, enantiomeric mixtures as well as optical isomers. The individual optical isomers can be prepared directly through asymmetric and/or stereospecific synthesis or by conventional chiral separation of optical isomers from the enantiomeric mixture.

In accordance with this invention, compounds of formula I are produced by the following reaction schemes (Schemes 1 and 2). The compounds of formula I can be prepared from compounds of formula 1 (obtained from commercial sources) and compounds of formula 2 (either obtained from commercial sources, or can be prepared as shown in Scheme 2) in three or four steps beginning with a regio- and stereo-selective ring opening of an epoxide of formula 2 with an appropriately substituted compound of formula 1 to produce compounds of formula 3 (Scheme 1). Any conventional method for the regio- and stereo-selective opening of an epoxide can be utilized for this conversion. In accordance with the preferred embodiment of this invention, compounds of formula 1 are heated with compounds of formula 2 at temperatures from 90° C. to 150° C. in the absence of solvent to afford compounds of formula 3. Compounds of formula 4a can be prepared from compounds of formula 3 via direct amidation with an appropriate amine. Any conventional method for direct conversion of an ester to an amide can be utilized for this conversion. In accordance with the preferred embodiment of this invention, compounds of formula 3 are heated in a sealed reaction vessel at temperatures between 50° C. to 100° C. with an excess of alcoholic amine to form compounds of formula 4a which can be reduced to form compounds of formula Ia. Any conventional method for reduction of an amide to an amine can be utilized for this conversion. In accordance with the preferred embodiment of this invention, compounds of formula 4a are heated with borane-tetrahydrofuran complex at temperatures between 60° C. and 80° C. to afford compounds of formula Ia, which can be converted to a pharmaceutically acceptable salt using any conventional method. Compounds of formula Ib can be prepared via N-alkylation of compounds of formula Ia. Any conventional method for N-alkylation of a secondary amine to a tertiary amine can be utilized for this conversion. In accordance with the preferred embodiment of this invention, compounds of formula Ia are heated with an aqueous solution of an aldehyde in the presence of formic acid at temperatures between 60° C. and 80° C. to afford compounds of formula Ib, which can be converted to a pharmaceutically acceptable salt using any conventional method. Alternatively, compounds of formula 4b can be prepared from compounds of formula 3 via direct amidation with a secondary amine. Any conventional method for direct conversion of an ester to a tertiary amide can be utilized for this conversion. In accordance with the preferred embodiment of this invention, compounds of formula 3 are heated in a sealed reaction vessel at temperatures between 50° C. to 100° C. with an excess of alcoholic secondary amine to form compounds of formula 4b which can be reduced to form compounds of formula Ib. Any conventional method for reduction of an amide to an amine can be utilized for this conversion. In accordance with the preferred embodiment of this invention, compounds of formula 4b are heated with borane-tetrahydrofuran complex at temperatures between 60° C. and 80° C. to afford compounds of formula Ib, which can be converted to a pharmaceutically acceptable salt using any conventional method.

Scheme 1

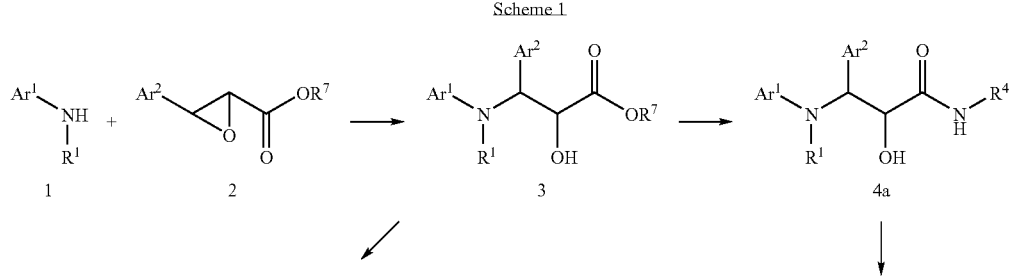

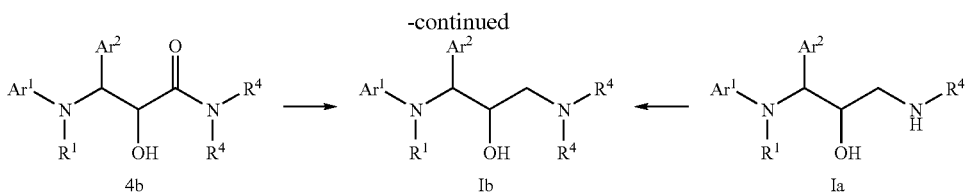

where: $R^7$ is $C_1$-$C_4$ lower alkyl.

Compounds of formula 2 can be obtained from commercial sources, or can be formed either racemically or asymmetrically using methods described in the literature starting with allylic esters 6. In accordance with the preferred embodiment of this invention, racemic epoxidation of the allylic ester 6 is conducted using di-(trifluoromethyl)dioxirane formed in-situ from trifluoroacetone and oxone (Yang, D.; Wong, M.-K.; Yip, *J. Org. Chem.* 1995, 60, 3887-3889). If it is desired to produce a single enantiomer of compounds of formula I, asymmetric epoxidation of an allylic ester 6 can be performed with oxone and a chiral ketone as reported in the literature (W-Y. Wu, X. She, Y. Shi, *J. Am. Chem. Soc.* 2002, 124, 8792). Allylic esters 6, if not commercially obtained, can be prepared from commercially obtained allylic carboxylic acids 5 by esterification. Any conventional method for esterification of a carboxylic acid to an ester can be utilized for this conversion. In accordance with the preferred embodiment of this invention, allylic carboxylic acids 5 are heated with an excess of alkyl iodide or alkyl bromide in the presence of cesium carbonate at temperatures between 60° C. and 80° C. to form allylic esters 6.

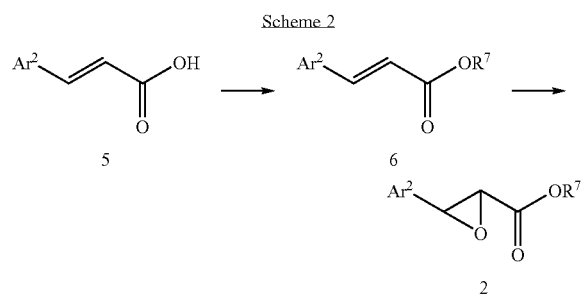

Scheme 2 where: $R^7$ is $C_1$-$C_4$ lower alkyl.

In other embodiments, the invention is directed to pharmaceutical compositions, comprising:
a. at least compound of formula I, or pharmaceutically acceptable salt thereof; and
b. at least one pharmaceutically acceptable carrier.

Generally, the compound of formula I, or a pharmaceutically acceptable salt thereof, will be present at a level of from about 0.1%, by weight, to about 90% by weight, based on the total weight of the pharmaceutical composition, based on the total weight of the pharmaceutical composition. Preferably, the compound of formula I, or a pharmaceutically acceptable salt thereof, will be present at a level of at least about 1%, by weight, based on the total weight of the pharmaceutical composition. More preferably, the compound of formula I, or a pharmaceutically acceptable salt thereof, will be present at a level of at least about 5%, by weight, based on the total weight of the pharmaceutical composition. Even more preferably, the norepinephrine reuptake inhibitor or a pharmaceutically acceptable salt thereof will be present at a level of at least about 10%, by weight, based on the total weight of the pharmaceutical composition. Yet even more preferably, the compound of formula I, or a pharmaceutically acceptable salt thereof, will be present at a level of at least about 25%, by weight, based on the total weight of the pharmaceutical composition.

Such compositions are prepared in accordance with acceptable pharmaceutical procedures, such as described in *Remington's Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups, and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions, which are sterile solutions or suspensions, can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

In another embodiment of the present invention, the compounds useful in the present invention may be administered to a mammal with one or more other pharmaceutical active agents such as those agents being used to treat any other medical condition present in the mammal. Examples of such pharmaceutical active agents include pain relieving agents, anti-angiogenic agents, anti-neoplastic agents, anti-diabetic agents, anti-infective agents, or gastrointestinal agents, or combinations thereof.

The one or more other pharmaceutical active agents may be administered in a therapeutically effective amount simultaneously (such as individually at the same time, or together in a pharmaceutical composition), and/or successively with one or more compounds of the present invention.

The term "combination therapy" refers to the administration of two or more therapeutic agents or compounds to treat a therapeutic condition or disorder described in the present disclosure, for example hot flush, sweating, thermoregulatory-related condition or disorder, or other. Such administration includes use of each type of therapeutic agent in a concurrent manner. In either case, the treatment regimen will provide beneficial effects of the drug combination in treating the conditions or disorders described herein.

The route of administration may be any route, which effectively transports the active compound of formula I, or a pharmaceutically acceptable salt thereof, to the appropriate or desired site of action, such as oral, nasal, pulmonary, transdermal, such as passive or iontophoretic delivery, or parenteral, e.g. rectal, depot, subcutaneous, intravenous, intraurethral, intramuscular, intranasal, ophthalmic solution or an ointment. Furthermore, the administration of compound of formula I, or pharmaceutically acceptable salt thereof, with other active ingredients may be concurrent or simultaneous.

It is believed that the present invention described presents a substantial breakthrough in the field of treatment, alleviation, inhibition, and/or prevention of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

Accordingly, in one embodiment, the present invention is directed to methods for treating or preventing a condition ameliorated by monoamine reuptake in a subject in need thereof, comprising the step of:
administering to said subject an effective amount of a compound of formula I or pharmaceutically acceptable salt thereof. The conditions ameliorated by monoamine reuptake include those selected from the group consisting of vasomotor symptoms, sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

In one embodiment, the present invention is directed to methods for treating or preventing vasomotor symptoms in a subject in need thereof, comprising the step of:
administering to said subject an effective amount of at least one compound of formula I or pharmaceutically acceptable salt thereof.

When estrogen levels are low or estrogen is absent, the normal levels between NE and 5-HT is altered and this altered change in neurotransmitter levels may result in changes in the sensitivity of the thermoregulatory center. The altered chemical levels may be translated in the thermoregulatory center as heat sensation and as a response, the hypothalamus may activate the descending autonomic pathways and result in heat dissipation via vasodilation and sweating (hot flush) (FIG. 1). Accordingly, the estrogen deprivation may result in altered norepinephrine activity.

Figure 2:
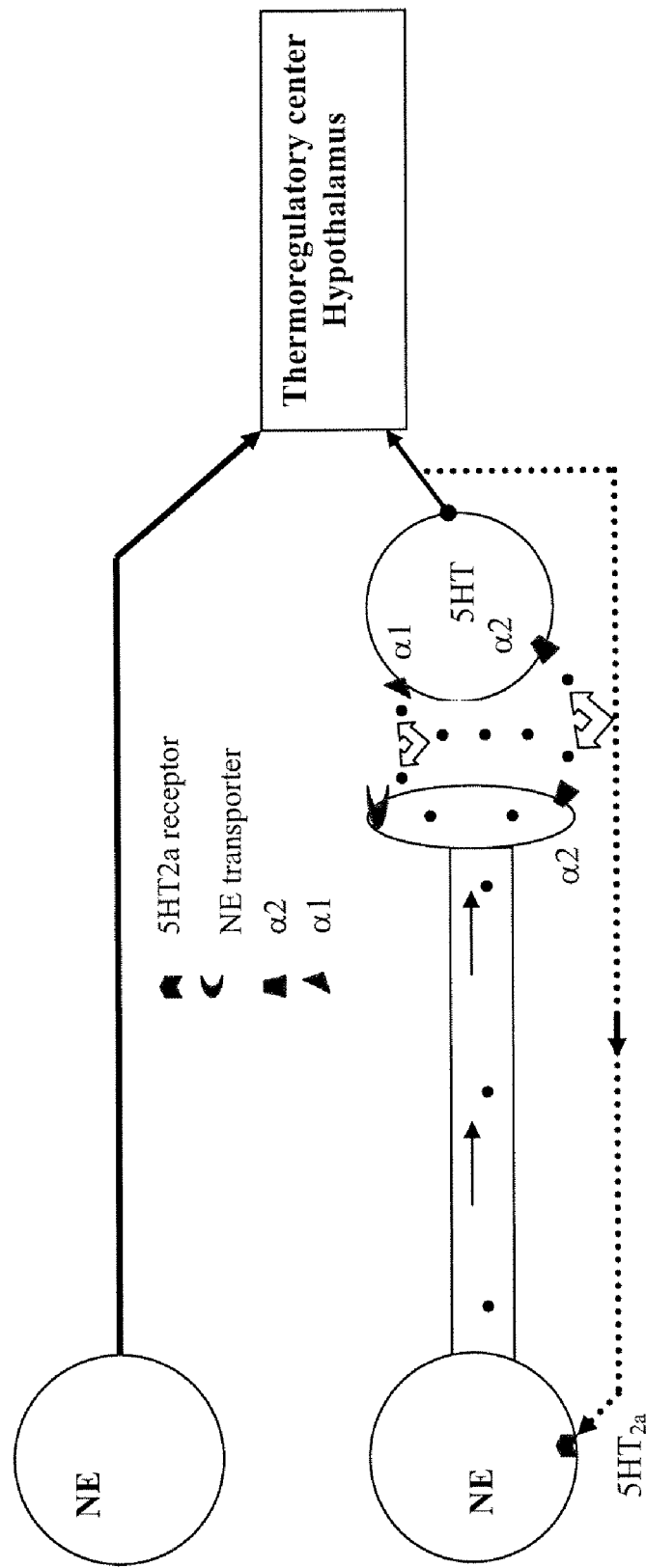
FIG. 2 is a schematic representation of the interactions of norepinephrine and serotonin and their respective receptors (5-HT$_{2a}$, $\alpha_1$ and $\alpha_2$-adrenergic).

Norepinephrine synthesized in perikarya of the brainstem is released at the nerve terminals in the hypothalamus and brainstem. In the hypothalamus, NE regulates the activity of neurons residing in the thermoregulatory center. In the brainstem, NE innervates serotoninergic neurons (5HT), and acting via adrenergic$_{\alpha 1}$ and adrenergic$_{\alpha 2}$ postsynaptic receptors, it stimulates the activity of the serotoninergic system. In response, 5-HT neurons also modulate the activity the thermoregulatory center and feedback to NE neurons. Via this feedback connection, 5-HT, acting via 5-HT$_{2a}$ receptors, inhibits the activity of NE neurons. Norepinephrine in the synaptic cleft is also taken up by NE transporter (NET) located in NE neurons. The transporter recycles NE and makes it available for multiple neurotransmission (FIG. 2).

The present invention provides a treatment for vasomotor symptoms by methods of recovering the reduced activity of norepinephrine. Norepinephrine activity in the hypothalamus or in the brainstem can be elevated by (i) blocking the activity of the NE transporter, (ii) blocking the activity of the presynaptic adrenergic$_{\alpha 2}$ receptor with an antagonist, or (iii) blocking the activity of 5-HT on NE neurons with a 5-HT$_{2a}$ antagonist.

In another embodiment, the present invention is directed to methods for treating or preventing a depression disorder in a subject in need thereof, comprising the step of:
administering to said subject an effective amount of at least one compound of formula I or pharmaceutically acceptable salt thereof.

In yet other embodiments, the present invention is directed to methods for treating or preventing sexual dysfunction in a subject in need thereof, comprising the step of:
administering to said subject an effective amount of at least one compound of formula I or pharmaceutically acceptable salt thereof.

In another embodiment, the present invention is directed to methods for treating or preventing gastrointestinal or genitourinary disorder, particularly stress incontinence or urge urinary incontinence, in a subject in need thereof, comprising the step of:
administering to said subject an effective amount of a compound of formula I or pharmaceutically acceptable salt thereof.

In another embodiment, the present invention is directed to methods for treating or preventing chronic fatigue syndrome in a subject in need thereof, comprising the step of:

administering to said subject an effective amount of a compound of formula I or pharmaceutically acceptable salt thereof.

In another embodiment, the present invention is directed to methods for treating or preventing fibromyalgia syndrome in a subject in need thereof, comprising the step of:

administering to said subject an effective amount of a compound of formula I or pharmaceutically acceptable salt thereof.

In further embodiments, the present invention is directed to methods for treating or preventing pain in a subject in need thereof, comprising the step of:

administering to said subject an effective amount of at least one compound of formula I or pharmaceutically acceptable salt thereof.

The pain may be, for example, acute pain (short duration) or chronic pain (regularly reoccurring or persistent). The pain may also be centralized or peripheral.

Examples of pain that can be acute or chronic and that can be treated in accordance with the methods of the present invention include inflammatory pain, musculoskeletal pain, bony pain, lumbosacral pain, neck or upper back pain, visceral pain, somatic pain, neuropathic pain, cancer pain, pain caused by injury or surgery such as burn pain or dental pain, or headaches such as migraines or tension headaches, or combinations of these pains. One skilled in the art will recognize that these pains may overlap one another. For example, a pain caused by inflammation may also be visceral or musculoskeletal in nature.

In a preferred embodiment of the present invention the compounds useful in the present invention are administered in mammals to treat chronic pain such as neuropathic pain associated for example with damage to or pathological changes in the peripheral or central nervous systems; cancer pain; visceral pain associated with for example the abdominal, pelvic, and/or perineal regions or pancreatitis; musculoskeletal pain associated with for example the lower or upper back, spine, fibromyalgia, temporomandibular joint, or myofascial pain syndrome; bony pain associated with for example bone or joint degenerating disorders such as osteoarthritis, rheumatoid arthritis, or spinal stenosis; headaches such migraine or tension headaches; or pain associated with infections such as HIV, sickle cell anemia, autoimmune disorders, multiple sclerosis, or inflammation such as osteoarthritis or rheumatoid arthritis.

In a more preferred embodiment, the compounds useful in this invention are used to treat chronic pain that is neuropathic pain, visceral pain, musculoskeletal pain, bony pain, cancer pain or inflammatory pain or combinations thereof, in accordance with the methods described herein. Inflammatory pain can be associated with a variety of medical conditions such as osteoarthritis, rheumatoid arthritis, surgery, or injury. Neuropathic pain may be associated with for example diabetic neuropathy, peripheral neuropathy, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, or nerve damage cause by injury resulting in peripheral and/or central sensitization such as phantom limb pain, reflex sympathetic dystrophy or postthoracotomy pain, cancer, chemical injury, toxins, nutritional deficiencies, or viral or bacterial infections such as shingles or HIV, or combinations thereof. The methods of use for compounds of this invention further include treatments in which the neuropathic pain is a condition secondary to metastatic infiltration, adiposis dolorosa, burns, or central pain conditions related to thalamic conditions.

As mentioned previously, the methods of the present invention may be used to treat pain that is somatic and/or visceral in nature. For example, somatic pain that can be treated in accordance with the methods of the present invention include pains associated with structural or soft tissue injury experienced during surgery, dental procedures, burns, or traumatic body injuries. Examples of visceral pain that can be treated in accordance with the methods of the present invention include those types of pain associated with or resulting from maladies of the internal organs such as ulcerative colitis, irritable bowel syndrome, irritable bladder, Crohn's disease, rheumatologic (arthralgias), tumors, gastritis, pancreatitis, infections of the organs, or biliary tract disorders, or combinations thereof. One skilled in the art will also recognize that the pain treated according to the methods of the present invention may also be related to conditions of hyperalgesia, allodynia, or both. Additionally, the chronic pain may be with or without peripheral or central sensitization.

The compounds useful in this invention may also be used to treat acute and/or chronic pains associated with female conditions, which may also be referred to as female-specific pain. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes.

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

(1RS,2SR)-3-amino-1-[methyl(phenyl)amino]-1-phenylpropan-2-ol hydrochloride

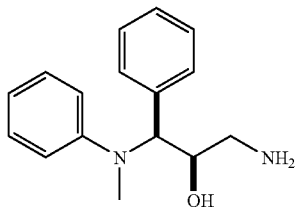

Step 1: A mixture of N-methylaniline (4.286 g 40.0 mmol) and ethyl trans-3-phenylglycidate (92% trans, 7.688 g, 40.00 mmol) was stirred at 135° C. for 3 hours. After cooling, the viscous liquid was purified via silica gel chromatography (3-15% EtOAc/hexane) and recrystallized (warm chloroform/hexane/−25° C.) to yield 10.90 g (91%) ethyl (2RS, 3RS)-2-hydroxy-3-[methyl(phenyl)amino]-3-phenylpropanoate as a white powder. MS (ESI) m/z 300 ([M+H]⁺); HRMS: calculated for $C_{18}H_{21}NO_3$+H, 300.1594; found (ESI, [M+H]⁺), 300.1594.

Step 2: A mixture of ethyl (2RS,3RS)-2-hydroxy-3-[methyl(phenyl)amino]-3-phenylpropanoate (1.20 g, 4.00 mmol) and methanolic ammonia solution (7 N, 20 mL) was stirred at 100° C. in a sealed tube for 5 hours. After cooling, all volatiles were removed under reduced pressure. The resulting yellow oil was purified via silica gel chromatography (15-30% iso-propanol/hexane) and recrystallized (warm ethyl acetate/hexane/−25° C.) to yield 582 mg (54%) of (2RS,3RS)-2-hydroxy-3-[methyl(phenyl)amino]-3-phenylpropanamide as white needles. MS (ESI) m/z 268.9 ([M−H]⁻); HRMS: calculated for $C_{16}H_{18}N_2O_2$+H, 271.1447; found (ESI, [M+H]⁺), 271.1458.

Step 3: A solution of (2RS,3RS)-2-hydroxy-3-[methyl(phenyl)amino]-3-phenylpropanamide (226 mg, 0.836 mmol) in dry tetrahydrofuran (2 mL) under nitrogen was treated slowly with a solution of borane (1.0 M in tetrahydrofuran, 4.20 mL, 4.20 mmol), and the resulting solution was stirred at 70° C. for 1 hour. After cooling in an ice bath, the reaction mixture was quenched with methanol (1 mL), followed by an aqueous hydrochloric acid solution (1N, 1 mL). The resulting mixture was stirred at 50° C. for 20 minutes. All volatiles were removed under reduced pressure. Water (10 mL) was added, and mixture was made alkaline using saturated aqueous potassium carbonate solution, and then extracted with ethyl acetate (15 mL). The organic layer was washed with water, brine, dried (anhydrous sodium sulfate) and concentrated under reduced pressure to yield 201 mg (94%) (1RS,2SR)-3-amino-1-[methyl(phenyl)amino]-1-phenylpropan-2-ol as a colorless oil. This oil was dissolved in ethanol (1 mL) and treated with a solution of hydrochloric acid (0.5 mL, 4M in 1,4-dioxane). All volatiles were again removed under reduced pressure. The resulting white solid was recrystallized (warm isopropanol/ethyl ether/−20° C.) to yield 225 mg (82%) of (1RS,2SR)-3-amino-1-[methyl(phenyl)amino]-1-phenylpropan-2-ol hydrochloride as a white powder. MS (ESI) m/z 257.0 ([M−H]⁺); HRMS: calculated for $C_{16}H_{20}N_2O$+H, 257.1648; found (ESI, [M+H]⁺), 257.1642.

Example 2

(1RS,2SR)-3-amino-1-[methyl(3-methylphenyl) amino]-1-phenylpropan-2-ol hydrochloride

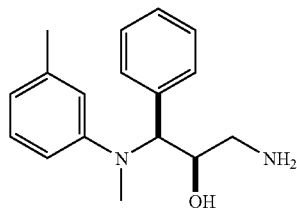

Step 1: In an analogous manner to Example 1, step 1, ethyl (2RS,3RS)-2-hydroxy-3-[methyl(3-methylphenyl)amino]-3-phenylpropanoate was prepared from N-methyl-3-toluidine and ethyl trans-3-phenylglycidate as a yellow oil. MS (ESI) m/z 314.0 ([M+H]⁺).

Step 2: In an analogous manner to Example 1, step 2, (2RS,3RS)-2-hydroxy-3-[methyl(3-methylphenyl)amino]-3-phenylpropanamide was prepared from ethyl (2RS,3RS)-2-hydroxy-3-[methyl(3-methylphenyl)amino]-3-phenylpropanoate as a white solid. MS (ESI) m/z 282.9 ([M−H]⁻).

Step 3: In an analogous manner to Example 1, step 3, (1RS,2SR)-3-amino-1-[methyl(3-methylphenyl)amino]-1-phenylpropan-2-ol hydrochloride was prepared from (2RS,3RS)-2-hydroxy-3-[methyl(3-methylphenyl)amino]-3-phenylpropanamide as a white solid. MS (ESI) m/z 271.0 ([M+H]⁺).

Example 3

(1RS,2SR)-3-amino-1-[(2-chlorophenyl)(methyl) amino]-1-phenylpropan-2-ol hydrochloride

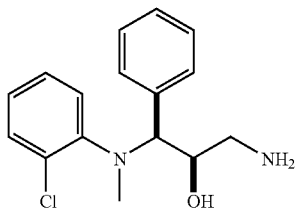

Step 1: In an analogous manner to Example 1, step 1, ethyl (2RS,3RS)-3-[(2-chlorophenyl)(methyl)amino]-2-hydroxy-3-phenylpropanoate was prepared from 2-choloro-N-methylaniline and ethyl trans-3-phenylglycidate as a colorless oil. MS (ESI) m/z 333.9 ([M+H]⁺).

Step 2: In an analogous manner to Example 1, step 2, (2RS,3RS)-3-[(2-chlorophenyl)(methyl)amino]-2-hydroxy-3-phenylpropanamide was prepared from ethyl (2RS,3RS)-3-[(2-chlorophenyl)(methyl)amino]-2-hydroxy-3-phenylpropanoate as an amorphous solid. MS (ESI) m/z 305 ([M+H]⁺).

Step 3: In an analogous manner to Example 1, step 3, (1RS,2SR)-3-amino-1-[(2-chlorophenyl)(methyl)amino]-1-phenylpropan-2-ol hydrochloride was prepared from (2RS,3RS)-3-[(2-chlorophenyl)(methyl)amino]-2-hydroxy-3-phenyl propanamide as a white solid. MS (ESI) m/z 291.0 ([M+H]⁺).

Example 4

(1RS,2SR)-3-amino-1-[(3-methoxyphenyl)(methyl) amino]-1-phenylpropan-2-ol hydrochloride

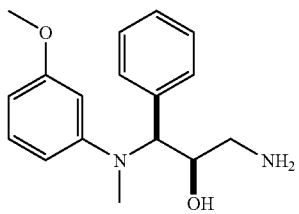

Step 1: In an analogous manner to Example 1, step 1, ethyl (2RS,3RS)-2-hydroxy-3-[(3-methoxyphenyl)(methyl) amino]-3-phenylpropanoate was prepared from 3-methoxy-N-methylaniline and ethyl trans-3-phenylglycidate as a colorless oil. MS (ESI) m/z 330.0 ([M+H]⁺).

Step 2: In an analogous manner to Example 1, step 2, (2RS,3RS)-2-hydroxy-3-[(3-methoxyphenyl)(methyl) amino]-3-phenylpropanamide was prepared from ethyl (2RS,3RS)-2-hydroxy-3-[(3-methoxyphenyl)(methyl)amino]-3-phenylpropanoate as a white solid. MS (ESI) m/z 301 ([M+H]⁺).

Step 3: In an analogous manner to Example 1, step 3, (1RS,2SR)-3-amino-1-[(3-methoxyphenyl)(methyl)amino]-

1-phenylpropan-2-ol hydrochloride was prepared from (2RS,3RS)-2-hydroxy-3-[(3-methoxyphenyl)(methyl)amino]-3-phenylpropanamide as a light green solid. MS (ESI) m/z 287.1 ([M+H]⁺).

Example 5

(1RS,2SR)-3-amino-1-(4-methoxyphenyl)-1-[methyl(phenyl) amino]propan-2-ol hydrochloride

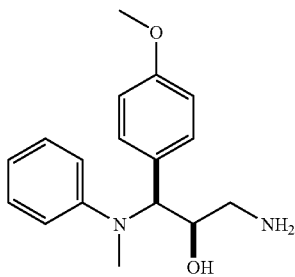

Step 1: In an analogous manner to Example 1, step 1, methyl (2RS,3RS)-2-hydroxy-3-(4-methoxyphenyl)-3-[methyl(phenyl)amino]propanoate was prepared from N-methylaniline and methyl trans-3-(4-methoxyphenyl)glycidate as an amber powder. MS (ESI) m/z 316 ([M+H]⁺); HRMS: calculated for $C_{18}H_{21}NO_4$+H, 316.1543; found (ESI, [M+H]⁺), 316.1548.

Step 2: In an analogous manner to Example 1, step 2, (2RS,3RS)-2-hydroxy-3-(4-methoxyphenyl)-3-[methyl(phenyl)amino]propanamide was prepared from methyl (2RS,3RS)-2-hydroxy-3-(4-methoxyphenyl )-3-[methyl(phenyl)amino]propanoate as a white amorphous solid. MS (ESI) m/z 298.8 ([M–H]⁻).

Step 3: In an analogous manner to Example 1, step 3, (1RS,2SR)-3-amino-1-(4-methoxyphenyl)-1-[methyl(phenyl)amino]propan-2-ol hydrochloride was prepared from (2RS,3RS)-2-hydroxy-3-(4-methoxyphenyl)-3-[methyl(phenyl)amino] propanamide as a white powder. MS (ESI) m/z 287 ([M+H]⁺); HRMS: calculated for $C_{17}H_{22}N_2O_2$+H, 287.1760; found (ESI, [M+H]⁺), 287.1774.

Example 6

(1RS,2SR)-3-amino-1-[(4-chlorophenyl)(methyl)amino]-1-(4-methoxyphenyl)propan-2-ol hydrochloride

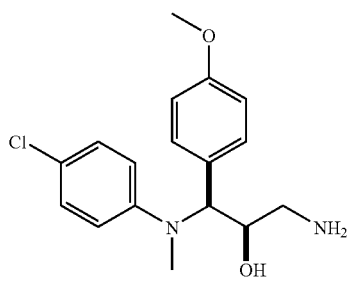

In an analogous manner to Example 1, step 1, methyl (2RS,3RS)-3-[(4-chlorophenyl)(methyl)amino]-2-hydroxy-3-(4-methoxyphenyl)propanoate was prepared from 4-chloro-N-methylaniline and methyl trans-3-(4-methoxyphenyl)glycidate as off-white crystals. MS (ESI) m/z 350 ([M+H]⁺); HRMS: calculated for $C_{18}H_{20}ClNO_4$+H, 350.1154; found (ESI, [M+H]⁺), 350.1161.

In an analogous manner to Example 1, step 2, (2RS,3RS)-3-[(4-chlorophenyl)(methyl)amino]-2-hydroxy-3-(4-methoxyphenyl)propanamide was prepared from methyl (2RS,3RS)-3-[(4-chlorophenyl)(methyl)amino]-2-hydroxy-3-(4-methoxyphenyl)propanoate as white needles.

In an analogous manner to Example 1, step 3, (1RS,2SR)-3-amino-1-[(4-chlorophenyl)(methyl)amino]-1-(4-methoxyphenyl)propan-2-ol hydrochloride was prepared from (2RS,3RS)-3-[(4-chlorophenyl)(methyl)amino]-2-hydroxy-3-(4-methoxyphenyl)propanamide as a white powder. MS (ESI) m/z 321.0 ([M+H]⁺); HRMS: calculated for $C_{17}H_{21}ClN_2O_2$+H, 321.1364; found (ESI, [M+H]⁺), 321.1380.

Example 7

(1RS,2SR)-3-amino-1-(3-fluorophenyl)-1-[methyl(phenyl) amino]propan-2-ol hydrochloride

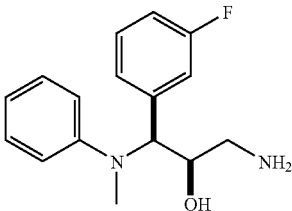

Step 1: To a mixture of trans-3-fluorocinnamic acid (50 g, 300 mmol) and iodomethane (300 mL) in acetone (1 L) was added portion wise cesium carbonate (147 g, 450 mmol, 1.5 equivalents), and the mixture was heated at 65° C. for 1.5 hours in a sealed reaction vessel. Upon cooling to room temperature, the reaction mixture was diluted with ethyl acetate (1 L), filtered through a pad of silica gel, and concentrated to give 47.33 g (87%) of trans-3-fluorocinnamic acid methyl ester as a colorless oil. MS (ES) m/z 180.0 (M⁺·).

Step 2: To a solution of trans-3-fluorocinnamic acid methyl ester (3.000 g, 16.65 mmol) in acetonitrile (130 mL) at 0° C. was added a solution of ethylenediaminetetraacetic acid disodium salt (0.4 M, 84 mL, 33.6 mmol, 2.0 equivalents), followed by cold (−30° C.) trifluoroacetone (20 mL, 224 mmol, 13.5 equivalents). To the resulting homogeneous solution was added a mixture of oxone (51.0 g, 82.96 mmol, 5 equivalents) and sodium bicarbonate (10.84 g, 129 mmol, 7.75 equivalents) portion wise over 1 hour. The reaction was then allowed to warm to ambient temperature and stirred overnight. The reaction mixture was poured into water (500 mL) and extracted with dichloromethane (3×100 mL). The combined organic extracts were dried (anhydrous sodium sulfate) and concentrated to give 3.22 g (99%) methyl trans-3-(3-fluorophenyl)glycidate as a colorless oil. MS (ESI) m/z 197.2 ([M+H]⁺).

Step 3: In an analogous manner to Example 1, step 1, methyl (2RS,3RS)-3-(3-fluorophenyl)-2-hydroxy-3-[methyl(phenyl)amino]propanoate was prepared from N-methylaniline and methyl trans-3-(3-fluorophenyl)glycidate as a tan powder. MS (ESI) m/z 304 ([M+H]⁺); HRMS: calculated for $C_{17}H_{18}FNO_3$+H, 304.1344; found (ESI, [M+H]⁺), 304.1332.

Step 4: In an analogous manner to Example 1, step 2, (2RS,3RS)-3-(3-fluorophenyl)-2-hydroxy-3-[methyl(phenyl)amino]propanamide was prepared from methyl (2RS,3RS)-3-(3-fluorophenyl)-2-hydroxy-3-[methyl(phenyl)amino]propanoate as a white amorphous powder. MS (ESI) m/z 289 ([M+H]⁺); HRMS: calculated for $C_{16}H_{17}FN_2O_2$+H, 289.1347; found (ESI, [M+H]⁺), 289.1345.

Step 5: In an analogous manner to Example 1, step 3, (1RS,2SR)-3-amino-1-(3-fluorophenyl)-1-[methyl(phenyl) amino]propan-2-ol hydrochloride was prepared from (2RS, 3RS)-3-(3-fluorophenyl)-2-hydroxy-3-[methyl(phenyl) amino] propanamide as a white powder. MS (ESI) m/z 275.0 ([M+H]$^+$); HRMS: calculated for $C_{16}H_{19}FN_2O+H$, 275.1554; found (ESI, [M+H]$^+$), 275.1553.

Example 8

(1RS,2SR)-3-(methylamino)-1-[methyl(phenyl) amino]-1-phenylpropan-2-ol hydrochloride

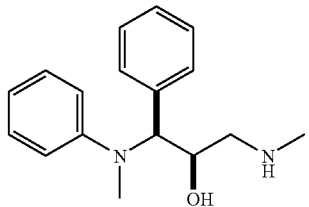

Step 1: A mixture of ethyl (2RS,3RS)-2-hydroxy-3-[methyl(phenyl)amino]-3-phenylpropanoate (Example 1, Step 1, 375 mg, 1.25 mmol) and ethanolic methylamine solution (33 weight % in absolute ethanol, 5 mL) was stirred at 80° C. in a sealed tube for 5 hours. After cooling, all volatiles were removed under reduced pressure. The resulting solid was recrystallized (warm chloroform/hexane/−25° C.) to yield 350 mg (99%) (2RS,3RS)-2-hydroxy-N-methyl-3-[methyl (phenyl)amino]-3-phenylpropanamide as white needles. MS (ESI) m/z 285 ([M+H]$^+$); HRMS: calculated for $C_{17}H_{20}N_2O_2+H$, 285.1598; found (ESI, [M+H]$^+$), 285.1592.

Step 2: In an analogous manner to Example 1, step 3, (1RS,2SR)-3-(methylamino)-1-[methyl(phenyl)amino]-1-phenylpropan-2-ol hydrochloride was prepared from (2RS, 3RS)-2-hydroxy-N-methyl-3-[methyl(phenyl)amino]-3-phenylpropanamide as a white powder. MS (ESI) m/z 271.3 ([M+H]$^+$); HRMS: calculated for $C_{17}H_{22}N_2O+H$, 271.1805; found (ESI, [M+H]$^+$), 271.1798.

Example 9

(1RS,2RS)-3-(methylamino)-1-[methyl(phenyl) amino]-1-phenylpropan-2-ol hydrochloride

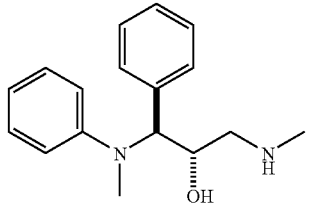

Ethyl (2SR,3RS)-2-hydroxy-3-[methyl(phenyl)amino]-3-phenylpropanoate was obtained as a minor product from the reaction of Example 1, step 1 as a viscous yellowish liquid. Yield: 470 mg (4%). MS (ESI) m/z 300.2 ([M+H]$^+$); HRMS: calculated for $C_{18}H_{21}NO_3+H$, 300.1594; found (ESI, [M+H]$^+$), 300.1601.

In an analogous manner to Example 8, step 1, (2SR,3RS)-2-hydroxy-N-methyl-3-[methyl(phenyl)amino]-3-phenyl-propanamide was prepared from ethyl (2SR,3RS)-2-hydroxy-3-[methyl(phenyl)amino]-3-phenylpropanoate as a white solid. MS (ESI) m/z 282.9 ([M−H]$^-$); HRMS: calculated for $C_{17}H_{20}N_2O_2+H$, 285.1598; found (ESI, [M+H]$^+$), 285.1607.

In an analogous manner to Example 1, step 3, (1RS,2RS)-3-(methylamino)-1-[methyl(phenyl)amino]-1-phenylpropan-2-ol hydrochloride was prepared from (2SR,3RS)-2-hydroxy-N-methyl-3-[methyl(phenyl)amino]-3-phenylpropanamide as a white powder. MS (ESI) m/z 271.0 ([M+H]$^+$); HRMS: calculated for $C_{17}H_{22}N_2O+H$, 271.1805; found (ESI, [M+H]$^+$), 271.1809.

Example 10

(1RS,2SR)-3-(methylamino)-1-[methyl(2-methylphenyl)amino]-1-phenylpropan-2-ol hydrochloride

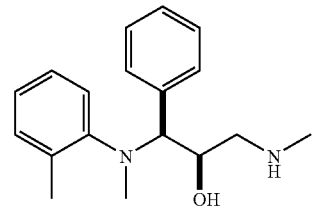

In an analogous manner to Example 1, step 1, ethyl (2RS, 3RS)-2-hydroxy-3-[methyl(2-methylphenyl)amino]-3-phenylpropanoate was prepared from N-methyl-o-toluidine and ethyl trans-3-phenylglycidate as a viscous yellowish liquid. MS (ESI) m/z 314.0 ([M+H]$^+$); HRMS: calculated for $C_{19}H_{23}NO_3+H$, 314.1751; found (ESI, [M+H]$^+$), 314.1753.

In an analogous manner to Example 8, step 1, (2RS,3RS)-2-hydroxy-N-methyl-3-[methyl(2-methylphenyl)amino]-3-phenylpropanamide was prepared from ethyl (2RS,3RS)-2-hydroxy-3-[methyl(2-methylphenyl)amino]-3-phenylpropanoate as a white solid. MS (ESI) m/z 299.0 ([M+H]$^+$); HRMS: calculated for $C_{18}H_{22}N_2O_2+H$, 299.1754; found (ESI, [M+H]$^+$), 299.1752.

In an analogous manner to Example b 1, step 3, (1RS,2SR)-3-(methylamino)-1-[methyl(2-methylphenyl)amino]-1-phenylpropan-2-ol hydrochloride was prepared from (2RS, 3RS)-2-hydroxy-N-methyl-3-[methyl(2-methylphenyl) amino]-3-phenyl propanamide as a white powder. HRMS: calculated for $C_{18}H_{24}N_2O+H$, 285.1961; found (ESI, [M+H]$^+$), 285.1974.

Example 11

(1RS,2SR)-3-(methylamino)-1-[methyl(3-methylphenyl)amino]-1-phenylpropan-2-ol hydrochloride

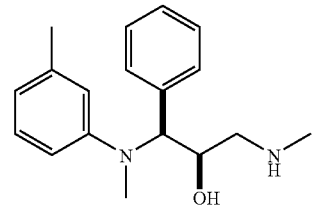

In an analogous manner to Example 8, step 1, (2RS,3RS)-2-hydroxy-N-methyl-3-[methyl(3-methylphenyl)amino]-3-phenylpropanamide was prepared from ethyl (2RS,3RS)-2- hydroxy-3-[methyl(3-methylphenyl)amino]-3-phenyl propanoate (Example 2, step 1) as a white solid. MS (ESI) m/z 296.9 ([M−H]⁻).

In an analogous manner to Example 1, step 3, (1RS,2SR)-3-(methylamino)-1-[methyl(3-methylphenyl)amino]-1-phenylpropan-2-ol hydrochloride was prepared from (2RS, 3RS)-2-hydroxy-N-methyl-3-[methyl(3-methylphenyl)amino]-3-phenyl propanamide as a brown solid. MS (ESI) m/z 285.0 ([M+H]⁺).

Example 12

(1RS,2SR)-3-(methylamino)-1-[methyl(4-methylphenyl)amino]-1-phenylpropan-2-ol hydrochloride

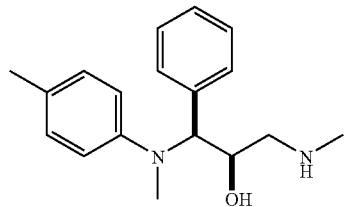

Step 1: In an analogous manner to Example 1, step 1, ethyl (2RS,3RS)-2-hydroxy-3-[methyl(4-methylphenyl)amino]-3-phenylpropanoate was prepared from N-methyl-p-toluidine and ethyl trans-3-phenylglycidate as a white solid. MS (ESI) m/z 314.0 ([M+H]⁺); HRMS: calculated for $C_{19}H_{23}NO_3$+H, 314.1751; found (ESI, [M+H]⁺), 314.1746.

Step 2: In an analogous manner to Example 8, step 1, (2RS,3RS)-2-hydroxy-N-methyl-3-[methyl(4-methylphenyl)amino]-3-phenylpropanamide was prepared from ethyl (2RS,3RS)-2-hydroxy-3-[methyl(4-methylphenyl)amino]-3-phenylpropanoate as a white solid. MS (ESI) m/z 299.0 ([M+H]⁺); HRMS: calculated for $C_{18}H_{22}N_2O_2$+H, 299.1754; found (ESI, [M+H]⁺), 299.1753.

Step 3: In an analogous manner to Example 1, step 3, (1RS,2SR)-3-(methylamino)-1-[methyl(4-methylphenyl)amino]-1-phenylpropan-2-ol hydrochloride was prepared from (2RS,3RS)-2-hydroxy-N-methyl-3-[methyl(4-methylphenyl)amino]-3-phenylpropanamide as a white powder. MS (ESI) m/z 285 ([M+H]⁺); HRMS: calculated for $C_{18}H_{24}N_2O$+H, 285.1961; found (ESI, [M+H]⁺), 285.1967.

Example 13

(1RS,2SR)-1-[(2-chlorophenyl)(methyl)amino]-3-(methylamino)-1-phenylpropan-2-ol hydrochloride

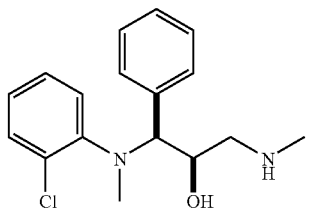

In an analogous manner to Example 8, step 1, (2RS,3RS)-3-[(2-chlorophenyl)(methyl)amino]-2-hydroxy-N-methyl-3-phenylpropanamide was prepared from ethyl (2RS,3RS)-3-[(2-chlorophenyl)(methyl)amino]-2-hydroxy-3-phenyl propanoate (Example 3, step 1) as an amorphous white solid. MS (ESI) m/z 318.9 ([M+H]⁺).

In an analogous manner to Example 1, step 3, (1RS,2SR)-1-[(2-chlorophenyl)(methyl)amino]-3-(methylamino)-1-phenylpropan-2-ol hydrochloride was prepared from (2RS, 3RS)-3-[(2-chlorophenyl)(methyl)amino]-2-hydroxy-N-methyl-3-phenylpropanamide as an amorphous off-white solid. MS (ESI) m/z 305.0 ([M+H]⁺).

Example 14

(1RS,2SR)-1-[(3-chlorophenyl)(methyl)amino]-3-(methylamino)-1-phenylpropan-2-ol hydrochloride

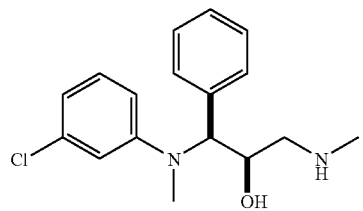

In an analogous manner to Example 1, step 1, ethyl (2RS,3RS)-3-[(3-chlorophenyl)(methyl)amino]-2-hydroxy-3-phenylpropanoate was prepared from 3-choloro-N-methylaniline and ethyl trans-3-phenylglycidate as a viscous yellowish liquid. MS (ESI) m/z 334.0 ([M+H]⁺); HRMS: calculated for $C_{18}H_{20}ClNO_3$+H, 334.1205; found (ESI, [M+H]⁺), 334.1196.

In an analogous manner to Example 8, step 1, (2RS,3RS)-3-[(3-chlorophenyl)(methyl)amino]-2-hydroxy-N-methyl-3-phenylpropanamide was prepared from ethyl (2RS,3RS)-3-[(3-chlorophenyl)(methyl)amino]-2-hydroxy-3-phenylpropanoate as a white solid. MS (ESI) m/z 316.9 ([M−H]⁻); HRMS: calculated for $C_{17}H_{19}ClN_2O_2$+H, 319.1208; found (ESI, [M+H]⁺), 319.1225.

In an analogous manner to Example 1, step 3, (1RS,2SR)-1-[(3-chlorophenyl)(methyl)amino]-3-(methylamino)-1-phenylpropan-2-ol hydrochloride was prepared from (2RS, 3RS)-3-[(3-chlorophenyl)(methyl)amino]-2-hydroxy-N-methyl-3-phenylpropanamide as a white powder. MS (ESI) m/z 305.0 ([M+H]⁺); HRMS: calculated for $C_{17}H_{21}ClN_2O$+H, 305.1415; found (ESI, [M+H]⁺), 305.1424.

Example 15

(1RS,2SR)-1-[(4-fluorophenyl)(methyl)amino]-3-(methylamino)-1-phenylpropan-2-ol hydrochloride

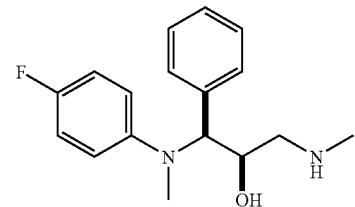

In an analogous manner to Example 1, step 1, ethyl (2RS, 3RS)-3-[(4-fluorophenyl)(methyl)amino]-2-hydroxy-3-phenylpropanoate was prepared from 4-fluoro-N-methylaniline and ethyl trans-3-phenylglycidate as a viscous yellowish liquid. MS (ESI) m/z 318 ([M+H]$^+$); HRMS: calculated for $C_{18}H_{20}FNO_3$+H, 318.1500; found (ESI, [M+H]$^+$), 318.1507.

In an analogous manner to Example 8, step 1, (2RS,3RS)-3-[(4-fluorophenyl)(methyl)amino]-2-hydroxy-N-methyl-3-phenylpropanamide was prepared from ethyl (2RS,3RS)-3-[(4-fluorophenyl)(methyl)amino]-2-hydroxy-3-phenylpropanoate as a white solid. MS (ESI) m/z 300.9 ([M−H]$^−$); HRMS: calculated for $C_{17}H_{19}FN_2O_2$+H, 303.1503; found (ESI, [M+H]$^+$), 303.1512.

In an analogous manner to Example 1, step 3, (1RS,2SR)-1-[(4-fluorophenyl)(methyl)amino]-3-(methylamino)-1-phenylpropan-2-ol hydrochloride was prepared from (2RS,3RS)-3-[(4-fluorophenyl)(methyl)amino]-2-hydroxy-N-methyl-3-phenylpropanamide as a white powder. MS (ESI) m/z 289.0 ([M+H]$^+$); HRMS: calculated for $C_{17}H_{21}FN_2O$+H, 289.1711; found (ESI, [M+H]$^+$), 289.1706.

Example 16

(1RS,2SR)-1-[(4-chlorophenyl)(methyl)amino]-3-(methylamino)-1-phenylpropan-2-ol hydrochloride

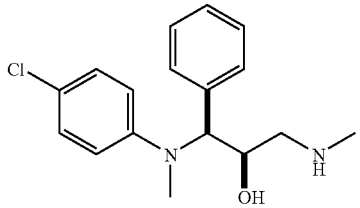

In an analogous manner to Example 1, step 1, ethyl (2RS,3RS)-3-[(4-chlorophenyl)(methyl)amino]-2-hydroxy-3-phenylpropanoate was prepared from 4-choloro-N-methylaniline and ethyl trans-3-phenylglycidate as a viscous yellowish liquid. MS (ESI) m/z 334 ([M+H]$^+$); HRMS: calculated for $C_{18}H_{20}ClNO_3$+H, 334.1205; found (ESI, [M+H]$^+$), 334.1211.

In an analogous manner to Example 8, step 1, (2RS,3RS)-3-[(4-chlorophenyl)(methyl)amino]-2-hydroxy-N-methyl-3-phenylpropanamide was prepared from ethyl (2RS,3RS)-3-[(4-chlorophenyl)(methyl)amino]-2-hydroxy-3-phenylpropanoate as a white solid. MS (ESI) m/z 316.9 ([M−H]$^−$); HRMS: calculated for $C_{17}H_{19}ClN_2O_2$+H, 319.1208; found (ESI, [M+H]$^+$), 319.1200.

In an analogous manner to Example 1, step 3, (1RS,2SR)-1-[(4-chlorophenyl)(methyl)amino]-3-(methylamino)-1-phenylpropan-2-ol hydrochloride was prepared from (2RS,3RS)-3-[(4-chlorophenyl)(methyl)amino]-2-hydroxy-N-methyl-3-phenylpropanamide as a white powder. MS (ESI) m/z 305.0 ([M+H]$^+$); HRMS: calculated for $C_{17}H_{21}ClN_2O$+H, 305.1415; found (ESI, [M+H]$^+$), 305.1415.

Example 17

(1RS,2SR)-1-[(3-methoxyphenyl)(methyl)amino]-3-(methylamino)-1-phenylpropan-2-ol hydrochloride

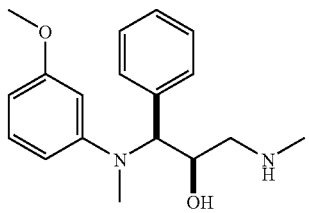

In an analogous manner to Example 8, step 1, (2RS,3RS)-2-hydroxy-3-[(3-methoxyphenyl)(methyl)amino]-N-methyl-3-phenylpropanamide was prepared from ethyl (2RS,3RS)-2-hydroxy-3-[(3-methoxyphenyl)(methyl)amino]-3-phenyl propanoate (Example 4, step 1) as a white solid. MS (ESI) m/z 315.0 ([M+H]$^+$).

In an analogous manner to Example 1, step 3, (1RS,2SR)-1-[(3-methoxyphenyl)(methyl)amino]-3-(methylamino)-1-phenylpropan-2-ol hydrochloride was prepared from (2RS,3RS)-2-hydroxy-3-[(3-methoxyphenyl)(methyl)amino]-N-methyl-3-phenylpropanamide as an amorphous light brown solid. MS (ESI) m/z 301 ([M+H]$^+$).

Example 18

(1RS,2SR)-1-[(4-methoxyphenyl)(methyl)amino]-3-(methylamino)-1-phenylpropan-2-ol hydrochloride

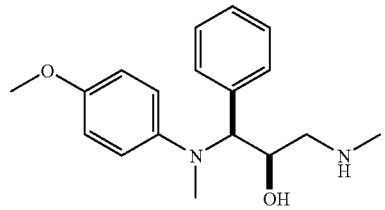

In an analogous manner to Example 1, step 1, ethyl (2RS,3RS)-2-hydroxy-3-[(4-methoxyphenyl)(methyl)amino]-3-phenylpropanoate was prepared from N-methyl-p-anisidine and ethyl trans-3-phenylglycidate as an amber powder. MS (ESI) m/z 330 ([M+H]$^+$); HRMS: calculated for $C_{19}H_{23}NO_4$+H, 330.1700; found (ESI, [M+H]$^+$), 330.1707.

In an analogous manner to Example 8, step 1, (2RS,3RS)-2-hydroxy-3-[(4-methoxyphenyl)(methyl)amino]-N-methyl-3-phenylpropanamide was prepared from ethyl (2RS,3RS)-2-hydroxy-3-[(4-methoxyphenyl)(methyl)amino]-3-phenylpropanoate as a white solid. MS (ESI) m/z 315.0 ([M+H]$^+$); HRMS: calculated for $C_{18}H_{22}N_2O_3$ +H, 315.1703; found (ESI, [M+H]$^+$), 315.1700.

In an analogous manner to Example 1, step 3, (1RS,2SR)-1-[(4-methoxyphenyl)(methyl)amino]-3-(methylamino)-1-phenylpropan-2-ol hydrochloride was prepared from (2RS,3RS)-2-hydroxy-3-[(4-methoxyphenyl)(methyl)amino]-N-methyl-3-phenylpropanamide as a white powder. MS (ESI) m/z 301.0 ([M+H]$^+$); HRMS: calculated for $C_{18}H_{24}N_2O_2$+H, 301.1911; found (ESI, [M+H]$^+$), 301.1937.

Example 19

(1RS,2SR)-1-(3-fluorophenyl)-3-(methylamino)-1-[methyl(phenyl)amino]propan-2-ol hydrochloride

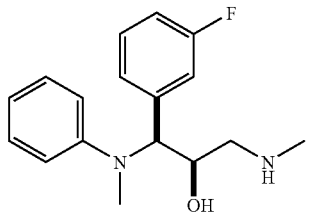

In an analogous manner to Example 8, step 1, (2RS,3RS)-3-(3-fluorophenyl)-2-hydroxy-N-methyl-3-[methyl(phenyl)amino]propanamide was prepared from methyl (2RS,3RS)-3-(3-fluorophenyl)-2-hydroxy-3-[methyl(phenyl)amino]propanoate (Example 7, step 3) as a white solid. MS (ESI) m/z 300.9 ([M−H]$^−$); HRMS: calculated for $C_{17}H_{19}FN_2O_2$+H, 303.1503; found (ESI, [M+H]$^+$), 303.1516.

In an analogous manner to Example 1, step 3, (1RS,2SR)-1-(3-fluorophenyl)-3-(methylamino)-1-[methyl(phenyl)amino]propan-2-ol hydrochloride was prepared from (2RS,3RS)-3-(3-fluorophenyl)-2-hydroxy-N-methyl-3-[methyl(phenyl)amino] propanamide as a white powder. MS (ESI) m/z 289.0 ([M+H]$^+$); HRMS: calculated for C$_{17}$H$_{21}$FN$_2$O+H, 289.1711; found (ESI, [M+H]$^+$), 289.1706.

Example 20

(1RS,2SR)-1-(3-chlorophenyl)-3-(methylamino)-1-[methyl(phenyl)amino]propan-2-ol hydrochloride

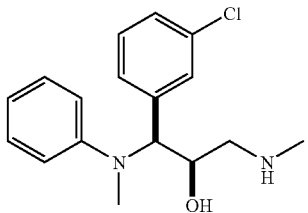

Step 1: In an analogous manner to Example 21, step 1, trans-3-chlorocinnamic acid ethyl ester was prepared from trans-3-chlorocinnamic acid as a colorless oil. MS (ESI) m/z 211.1 ([M+H]$^+$).

Step 2: In an analogous manner to Example 7, step 2, ethyl trans-3-(3-chlorophenyl)glycidate was prepared from trans-3-chlorocinnamic acid ethyl ester as a colorless oil. MS (ESI) m/z 268.0 ([M+H+ACN]$^+$).

Step 3: In an analogous manner to Example 1, step 1, ethyl (2RS,3RS)-3-(3-chlorophenyl)-2-hydroxy-3-[methyl(phenyl)amino]propanoate was prepared from N-methylaniline and ethyl trans-3-(3-chlorophenyl)glycidate as a white solid. MS (ESI) m/z 334.1 ([M+H]$^+$).

Step 4: In an analogous manner to Example 8, step 1, (2RS,3RS)-3-(3-chlorophenyl)-2-hydroxy-N-methyl-3-[methyl(phenyl)amino]propanamide was prepared from ethyl (2RS,3RS)-3-(3-chlorophenyl)-2-hydroxy-3-[methyl(phenyl)amino]propanoate as a white solid. MS (ESI) m/z 319.5 ([M+H]$^+$).

Step 5: In an analogous manner to Example 1, step 3, (1RS,2SR)-1-(3-chlorophenyl)-3-(methylamino)-1-[methyl(phenyl)amino]propan-2-ol hydrochloride was prepared from (2RS,3RS)-3-(3-chlorophenyl)-2-hydroxy-N-methyl-3-[methyl(phenyl)amino]propanamide as a white powder. MS (ESI) m/z 305.0 ([M+H]$^+$); HRMS: calculated for C$_{17}$H$_{21}$ClN$_2$O+H, 305.1415; found (ESI, [M+H]$^+$), 305.1416.

Example 21

(1RS,2SR)-1-(4-chlorophenyl)-3-(methylamino)-1-[methyl(phenyl)amino]propan-2-ol hydrochloride

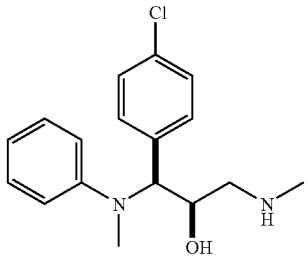

Step 1: To a solution of trans-4-chlorocinnamic acid (10 g, 55 mmol) in ethanol (60 mL) was added a catalytic amount of concentrated sulfuric acid (2-3 drops), and the mixture was heated (70° C.) until a majority of the starting material was consumed as evidenced by LCMS. The reaction mixture was concentrated and the contents were redissolved in ethyl acetate. The organic phase was extracted with an aqueous solution of sodium bicarbonate (5%, 3×) followed by a brine wash. The organic phase was dried (MgSO$_4$), filtered and concentrated to afford trans-4-chlorocinnamic acid ethyl ester as a colorless oil. MS (ESI) m/z 211.1 ([M+H]$^+$).

Step 2: In an analogous manner to Example 7, step 2, ethyl trans-3-(4-chlorophenyl)glycidate was prepared from trans-4-chlorocinnamic acid ethyl ester as a colorless oil. MS (ESI) m/z 268.1 ([M+H+ACN]$^+$).

Step 3: In an analogous manner to Example 1, step 1, ethyl (2RS,3RS)-3-(4-chlorophenyl)-2-hydroxy-3-[methyl(phenyl)amino]propanoate was prepared from N-methylaniline and ethyl trans-3-(4-chlorophenyl)glycidate as a white solid. MS (ESI) m/z 334.0 ([M+H]$^+$).

Step 4: In an analogous manner to Example 8, step 1, (2RS,3RS)-3-(4-chlorophenyl)-2-hydroxy-N-methyl-3-[methyl(phenyl)amino]propanamide was prepared from ethyl (2RS,3RS)-3-(4-chlorophenyl)-2-hydroxy-3-[methyl(phenyl)amino]propanoate as a white solid. MS (ESI) m/z 319.5 ([M+H]$^+$).

Step 5: In an analogous manner to Example 1, step 3, (1RS,2SR)-1-(4-chlorophenyl)-3-(methylamino)-1-[methyl(phenyl)amino]propan-2-ol hydrochloride was prepared from (2RS,3RS)-3-(4-chlorophenyl)-2-hydroxy-N-methyl-3-[methyl(phenyl)amino]propanamide as a white powder. MS (ESI) m/z 305.0 ([M+H]$^+$); HRMS: calculated for C$_{17}$H$_{21}$ClN$_2$O+H, 305.1415; found (ESI, [M+H]$^+$), 305.1419.

Example 22

(1RS,2SR)-1-(4-methoxyphenyl)-3-(methylamino)-1-[methyl(phenyl)amino]propan-2-ol hydrochloride

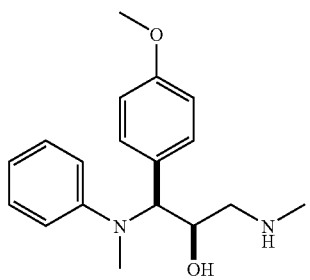

In an analogous manner to Example 8, step 1, (2RS,3RS)-2-hydroxy-3-(4-methoxyphenyl)-N-methyl-3-[methyl(phenyl)amino]propanamide was prepared from methyl (2RS,3RS)-2-hydroxy-3-(4-methoxyphenyl)-3-[methyl(phenyl)amino] propanoate (Example 5, step 1) as a white solid.

In an analogous manner to Example 1, step 3, (1RS,2SR)-1-(4-methoxyphenyl)-3-(methylamino)-1-[methyl(phenyl)amino]propan-2-ol hydrochloride was prepared from (2RS,3RS)-2-hydroxy-3-(4-methoxyphenyl)-N-methyl-3-[methyl(phenyl)amino]propanamide as a white powder. MS (ESI) m/z 301 ([M+H]$^+$); HRMS: calculated for C$_{18}$H$_{24}$N$_2$O$_2$+H, 301.1916; found (ESI, [M+H]$^+$), 301.1929.

Example 23

(1RS,2SR)-1-[(4-chlorophenyl)(methyl)amino]-1-(3-fluorophenyl)-3-(methylamino)propan-2-ol hydrochloride

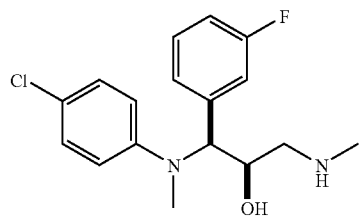

In an analogous manner to Example 1, step 1, methyl (2RS,3RS)-3-[(4-chlorophenyl)(methyl)amino]-3-(3-fluorophenyl)-2-hydroxy-propanoate was prepared from 4-chloro-N-methylaniline and methyl trans-3-(3-fluorophenyl)glycidate (Example 7, step 2) as a white solid.

In an analogous manner to Example 8, step 1, (2RS,3RS)-3-[(4-chlorophenyl)(methyl)amino]-3-(3-fluorophenyl)-2-hydroxy-N-methylpropanamide was prepared from methyl (2RS,3RS)-3-[(4-chlorophenyl)(methyl)amino]-3-(3-fluorophenyl)-2-hydroxy-propanoate as a white solid. MS (ESI) m/z 334.9 ([M−H]$^-$); HRMS: calculated for $C_{17}H_{18}ClFN_2O_2$+H, 337.1114; found (ESI, [M+H]$^+$), 337.1126.

In an analogous manner to Example 1, step 3, (1RS,2SR)-1-[(4-chlorophenyl)(methyl)amino]-1-(3-fluorophenyl)-3-(methylamino)propan-2-ol hydrochloride was prepared from (2RS,3RS)-3-[(4-chlorophenyl)(methyl)amino]-3-(3-fluorophenyl)-2-hydroxy-N-methylpropanamide as a white powder. MS (ESI) m/z 323.0 ([M+H]$^+$); HRMS: calculated for $C_{17}H_{20}ClFN_2O$+H, 323.1321; found (ESI, [M+H]$^+$), 323.1329.

Example 24

(1RS,2SR)-1-[(3-fluorophenyl)(methyl)amino]-1-(4-methoxyphenyl)-3-(methylamino)propan-2-ol hydrochloride

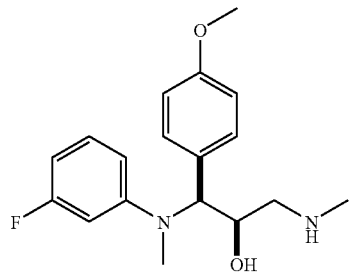

In an analogous manner to Example 1, step 1, methyl (2RS,3RS)-3-[(3-fluorophenyl)(methyl)amino]-2-hydroxy-3-(4-methoxyphenyl)propanoate was prepared from 3-fluoro-N-methylaniline and methyl trans-3-(4-methoxyphenyl)glycidate as a white solid. MS (ESI) m/z 334 ([M−H]$^-$); HRMS: calculated for $C_{18}H_{20}FNO_4$+H, 334.1449; found (ESI, [M+H]$^+$), 334.1460.

In an analogous manner to Example 8, step 1, (2RS,3RS)-3-[(3-fluorophenyl)(methyl)amino]-2-hydroxy-3-(4-methoxyphenyl)-N-methylpropanamide was prepared from methyl (2RS,3RS)-3-[(3-fluorophenyl)(methyl)amino]-2-hydroxy-3-(4-methoxyphenyl)propanoate as a white solid. MS (ESI) m/z 331.0 ([M−H]$^-$); HRMS: calculated for $C_{18}H_{21}FN_2O_3$+H, 333.1609; found (ESI, [M+H]$^+$), 333.1626.

In an analogous manner to Example 1, step 3, (1RS,2SR)-1-[(3-fluorophenyl)(methyl)amino]-1-(4-methoxyphenyl)-3-(methylamino)propan-2-ol hydrochloride was prepared from (2RS,3RS)-3-[(3-fluorophenyl)(methyl)amino]-2-hydroxy-3-(4-methoxyphenyl)-N-methylpropanamide as a white powder. MS (ESI) m/z 319.1 ([M+H]$^+$); HRMS: calculated for $C_{18}H_{23}FN_2O_2$+H, 319.1822; found (ESI, [M+H]$^+$), 319.1834.

Example 25

(1RS,2SR)-1-[(4-chlorophenyl)(methyl)amino]-1-(4-methoxyphenyl)-3-(methylamino)propan-2-ol hydrochloride

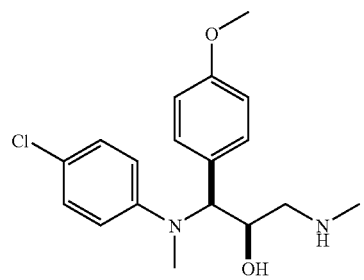

In an analogous manner to Example 1, step 1, methyl (2RS,3RS)-3-[(4-chlorophenyl)(methyl)amino]-2-hydroxy-3-(4-methoxyphenyl)propanoate was prepared from 4-chloro-N-methylaniline and methyl trans-3-(4-methoxyphenyl)glycidate as a white solid. MS (ESI) m/z 350 ([M+H]$^+$); HRMS: calculated for $C_{18}H_{20}ClNO_4$+H, 350.1154; found (ESI, [M+H]$^+$), 350.1161.

In an analogous manner to Example 8, step 1, (2RS,3RS)-3-[(4-chlorophenyl)(methyl)amino]-2-hydroxy-3-(4-methoxyphenyl)-N-methylpropanamide was prepared from methyl (2RS,3RS)-3-[(4-chlorophenyl)(methyl)amino]-2-hydroxy-3-(4-methoxyphenyl)propanoate as a white solid. MS (ESI) m/z 346.7 ([M−H]$^-$).

In an analogous manner to Example 1, step 3, (1RS,2SR)-1-[(4-chlorophenyl)(methyl)amino]-1-(4-methoxyphenyl)-3-(methylamino)propan-2-ol hydrochloride was prepared from (2RS,3RS)-3-[(4-chlorophenyl)(methyl)amino]-2-hydroxy-3-(4-methoxyphenyl)-N-methylpropanamide as a white powder. MS (ESI) m/z 335 ([M+H]$^+$); HRMS: calculated for $C_{18}H_{23}ClN_2O_2$+H, 335.1521; found (ESI, [M+H]$^+$), 335.1512.

Example 26

(1RS,2SR)-1-(4-methoxyphenyl)-1-[(4-methoxyphenyl)(methyl)amino]-3-(methylamino)propan-2-ol hydrochloride

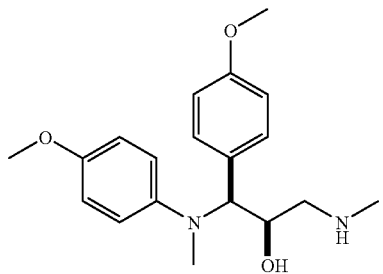

In an analogous manner to Example 1, step 1, methyl (2RS,3RS)-2-hydroxy-3-(4-methoxyphenyl-3-[(4-methoxyphenyl)(methyl)amino]propanoate was prepared from N-methyl-p-anisidine and methyl trans-3-(4-methoxyphenyl)glycidate as a white solid. MS (ESI) m/z 346 ([M+H]$^+$); HRMS: calculated for $C_{19}H_{23}NO_5$+H, 346.1649; found (ESI, [M+H]$^+$), 346.1657.

In an analogous manner to Example 8, step 1, (2RS,3RS)-2-hydroxy-3-(4-methoxyphenyl)-3-[(4-methoxyphenyl)(methyl)amino]-N-methylpropanamide was prepared from methyl (2RS,3RS)-2-hydroxy-3-(4-methoxyphenyl)-3-[(4-methoxyphenyl)(methyl)amino]propanoate as a white solid. (ESI) m/z 345.1 ([M+H]$^+$); HRMS: calculated for $C_{19}H_{24}N_2O_4$+H, 345.1809; found (ESI, [M+H]$^+$), 345.1809.

In an analogous manner to Example 1, step 3, (1RS,2SR)-1-(4-methoxyphenyl)-1-[(4-methoxyphenyl)(methyl)amino]-3-(methylamino)propan-2-ol hydrochloride was prepared from (2RS,3RS)-2-hydroxy-3-(4-methoxyphenyl)-3-[(4-methoxyphenyl)(methyl)amino]-N-methylpropanamide as a white powder. MS (ESI) m/z 331.1 ([M+H]$^+$); HRMS: calculated for $C_{19}H_{26}N_2O_3$+H, 331.2016; found (ESI, [M+H]$^+$), 331.2010.

Example 27

(1RS,2SR)-3-(methylamino)-1-[methyl(1-naphthyl)amino]-1-phenylpropan-2-ol hydrochloride

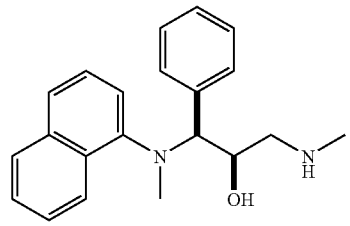

In an analogous manner to Example 1, step 1, ethyl (2RS,3RS)-2-hydroxy-3-[methyl(1-naphthyl)amino]-3-phenylpropanoate was prepared from N-methyl-1-naphthylamine (prepared by basification of commercially available N-methyl-1-naphthylamine hydrochloride salt) and ethyl trans-3-phenylglycidate as a dark oil. MS (ESI) m/z 350 ([M+H]$^+$); HRMS: calculated for $C_{22}H_{23}NO_3$+H, 350.1751; found (ESI, [M+H]$^+$), 350.1755.

In an analogous manner to Example 8, step 1, (2RS,3RS)-2-hydroxy-N-methyl-3-[methyl(1-naphthyl)amino]-3-phenylpropanamide was prepared from ethyl (2RS,3RS)-2-hydroxy-3-[methyl(1-naphthyl)amino]-3-phenylpropanoate as a white solid. (ESI) m/z 335 ([M+H]$^+$); HRMS: calculated for $C_{21}H_{22}N_2O_2$+H, 335.1760; found (ESI, [M+H]$^+$), 335.1747.

In an analogous manner to Example 1, step 3, (1RS,2SR)-3-(methylamino)-1-[methyl(1-naphthyl)amino]-1-phenylpropan-2-ol hydrochloride was prepared from (2RS,3RS)-2-hydroxy-N-methyl-3-[methyl(1-naphthyl)amino]-3-phenylpropanamide as a white powder. MS (ESI) m/z 321 ([M+H]$^+$); HRMS: calculated for $C_{21}H_{24}N_2O$+H, 321.1961; found (ESI, [M+H]$^+$), 321.1950.

Example 28

(1RS,2SR)-3-(ethylamino)-1-[methyl(4-methylphenyl)amino]-1-phenylpropan-2-ol hydrochloride

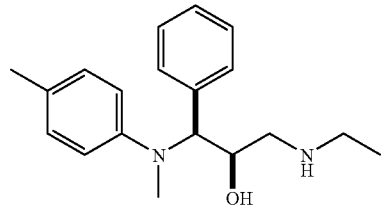

Step 1: A mixture of ethyl (2RS,3RS)-2-hydroxy-3-[methyl(4-methylphenyl)amino]-3-phenylpropanoate (Example 12, step 1, 948 mg, 3.03 mmol) and methanolic ethylamine solution (2.0 M in methanol, 25 mL) was stirred at 120° C. in a sealed tube for 48 hours. After cooling, all volatiles were removed under reduced pressure. The crude product was purified by flash column chromatography (silica gel, 0-15% ethyl acetate/hexane) and recrystallized (warm chloroform/hexane/−25° C.) to yield 537 mg (57%) of (2RS,3RS)-N-ethyl-2-hydroxy-3-[methyl(4-methylphenyl)amino]-3-phenylpropanamide as a white solid. MS (ESI) m/z 313 ([M+H]$^+$); HRMS: calculated for $C_{19}H_{24}N_2O_2$+H, 313.1911; found (ESI, [M+H]$^+$), 313.1908.

Step 2: In an analogous manner to Example 1, step 3, (1RS,2SR)-3-(ethylamino)-1-[methyl(4-methylphenyl)amino]-1-phenylpropan-2-ol hydrochloride was prepared from (2RS,3RS)-N-ethyl-2-hydroxy-3-[methyl(4-methylphenyl)amino]-3-phenylpropanamide as a white powder. MS (ESI) m/z 299.2 ([M+H]$^+$); HRMS: calculated for $C_{19}H_{26}N_2O$+H, 299.2118; found (ESI, [M+H]$^+$), 299.2115.

Example 29

(1RS,2SR)-1-[(4-chlorophenyl)(methyl)amino]-3-(ethylamino)-1-(4-methoxyphenyl)propan-2-ol hydrochloride

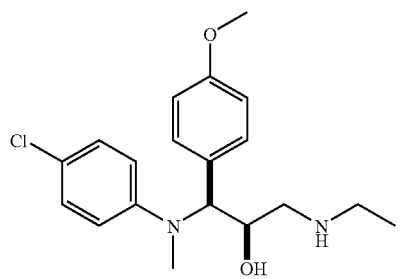

In an analogous manner to Example 28, step 1, (2RS,3RS)-3-[(4-chlorophenyl)(methyl)amino]-2-hydroxy-3-(4-methoxyphenyl)-N-ethylpropanamide was prepared from methyl (2RS,3RS)-3-[(4-chlorophenyl)(methyl)amino]-2-hydroxy-3-(4-methoxyphenyl)propanoate (Example 6, step 1) as a white solid.

In an analogous manner to Example 1, step 3, (1RS,2SR)-1-[(4-chlorophenyl)(methyl)amino]-3-(ethylamino)-1-(4- methoxyphenyl)propan-2-ol hydrochloride was prepared from (2RS,3RS)-3-[(4-chlorophenyl)(methyl)amino]-2-hydroxy-3-(4-methoxyphenyl)-N-ethylpropanamide as a white powder. MS (ESI) m/z 349.1 ([M+H]$^+$); HRMS: calculated for $C_{19}H_{25}ClN_2O_2$+H, 349.1677; found (ESI, [M+H]$^+$), 349.1671.

Example 30

(1RS,2SR)-1-(3-chlorophenyl)-3-(ethylamino)-1-[methyl(phenyl)amino]propan-2-ol hydrochloride

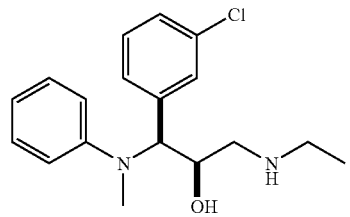

In an analogous manner to Example 28, step 1, (2RS,3RS)-3-(3-chlorophenyl)-2-hydroxy-N-ethyl-3-[methyl(phenyl)amino]propanamide was prepared from ethyl (2RS,3RS)-3-(3-chlorophenyl)-2-hydroxy-3-[methyl(phenyl)amino]propanoate (Example 20, step 3) as a white solid. MS (ESI) m/z 331.0 ([M–H]$^-$).

In an analogous manner to Example 1, step 3, (1RS,2SR)-1-(3-chlorophenyl)-3-(ethylamino)-1-[methyl(phenyl)amino]propan-2-ol hydrochloride was prepared from (2RS,3RS)-3-(3-chlorophenyl)-2-hydroxy-N-ethyl-3-[methyl(phenyl)amino]propanamide as a white powder. MS (ESI) m/z 319.0 ([M+H]$^+$); HRMS: calculated for $C_{18}H_{23}ClN_2O$+H, 319.1572; found (ESI, [M+H]$^+$), 319.1566.

Example 31

(1RS,2SR)-1-(4-chlorophenyl)-3-(ethylamino)-1-[methyl(phenyl)amino]propan-2-ol hydrochloride

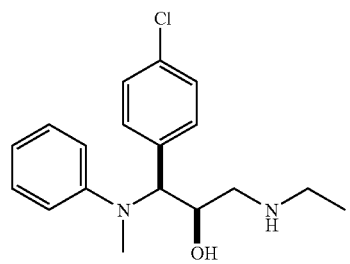

In an analogous manner to Example 28, step 1, (2RS,3RS)-3-(4-chlorophenyl)-2-hydroxy-N-ethyl-3-[methyl(phenyl)amino]propanamide was prepared from ethyl (2RS,3RS)-3-(4-chlorophenyl)-2-hydroxy-3-[methyl(phenyl)amino]propanoate (Example 21, step 3) as a white solid. MS (ESI) m/z 331.0 ([M–H]$^-$).

In an analogous manner to Example 1, step 3, (1RS,2SR)-1-(4-chlorophenyl)-3-(ethylamino)-1-[methyl(phenyl)amino]propan-2-ol hydrochloride was prepared from (2RS,3RS)-3-(4-chlorophenyl)-2-hydroxy-N-ethyl-3-[methyl(phenyl)amino] propanamide as a white powder. MS (ESI) m/z 319.0 ([M+H]$^+$); HRMS: calculated for $C_{18}H_{23}ClN_2O$+H, 319.1572; found (ESI, [M+H]$^+$), 319.1579.

Example 32

(1RS,2SR)-3-(dimethylamino)-1-[methyl (4-methylphenyl) amino]-1-phenylpropan-2-ol hydrochloride

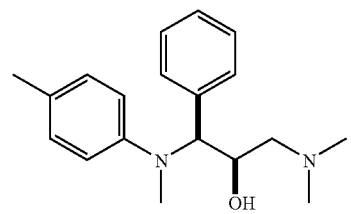

To a mixture of (1RS,2SR)-3-(methylamino)-1-[methyl(4-methylphenyl)amino]-1-phenylpropan-2-ol hydrochloride (Example 12, 83 mg, 0.23 mmol) in formic acid (0.4 mL) at 50° C., was added an aqueous solution of formaldehyde (37% in water, 0.16 mL). The reaction was heated at 70° C. for 1 hour, then poured into water (10 mL) and basified to pH 10 with the addition of an aqueous solution of sodium hydroxide (2 N). The product was extracted with ethyl acetate (3×10 mL), and the combined organic extracts were dried (anhydrous sodium sulfate) and concentrated to yield 59 mg (86%) 1RS,2SR)-3-(dimethylamino)-1-[methyl(4-methylphenyl)amino]-1-phenylpropan-2-ol as a viscous, colorless liquid. The product was dissolved in ethanol (0.5 mL) and treated with a solution of hydrochloric acid (0.1 mL, 4 M in 1,4-dioxane). All volatiles were again removed under reduced pressure. The resulting white solid was recrystallized (isopropanol/ethyl ether/–20° C.) to yield 64 mg (75%) of (1RS,2SR)-3-(dimethylamino)-1-[methyl(4-methylphenyl)amino]-1-phenylpropan-2-ol hydrochloride as a white powder. MS (ESI) m/z 299.1 ([M–H]$^+$); HRMS: calculated for $C_{19}H_{26}N_2O$+H, 299.2118; found (ESI, [M+H]$^+$), 299.2109.

Cell Lines, Culture Reagents, and Assays

MDCK-Net6 cells, stably transfected with human hNET (Pacholczyk, T., R. D. Blakely, and S. G. Amara, Nature, 1991, 350(6316): p. 350-4) were cultured in growth medium containing high glucose DMEM (Gibco, Cat. No. 11995), 10% FBS (dialyzed, heat-inactivated, US Bio-Technologies, Lot FBD1129HI) and 500 μg/ml G418 (Gibco, Cat. No. 10131). Cells were plated at 300,000 T75 flask and cells were split twice weekly. The JAR cell line (human placental choriocarcinoma) was purchased from ATCC (Cat. No. HTB-144). The cells were cultured in growth medium containing RPMI 1640 (Gibco, Cat. No. 72400), 10% FBS (Irvine, Cat. No. 3000), 1% sodium pyruvate (Gibco, Cat. No. 1136) and 0.25% glucose. Cells were plated at 250,000 cells/T75 flask and split twice weekly. For all assays, cells were plated in Wallac 96-well sterile plates (PerkinElmer, Cat. No. 3983498).

Norepinephrine (NE) Uptake Assay

On day 1, cells were plated at 3,000 cells/well in growth medium and maintained in a cell incubator (37° C., 5% $CO_2$). On day 2, growth medium was replaced with 200 pl of assay buffer (25 mM HEPES; 120 mM NaCl; 5 mM KCl; 2.5 mM $CaCl_2$; 1.2 mM $MgSO_4$; 2 mg/ml glucose (pH 7.4, 37° C.)) containing 0.2 mg/ml ascorbic acid and 10 pM pargyline.

Plates containing cells with 200 μl of assay buffer were equilibrated for 10 minutes at 37° C. prior to addition of compounds. A stock solution of desipramine was prepared in DMSO (10 mM) and delivered to triplicate wells containing cells for a final test concentration of 1 μM. Data from these wells were used to define non-specific NE uptake (minimum NE uptake). Test compounds were prepared in DMSO (10 mM) and diluted in assay buffer according to test range (1 to 10,000 nM). Twenty-five microliters of assay buffer (maximum NE uptake) or test compound were added directly to triplicate wells containing cells in 200 μl of assay buffer. The cells in assay buffer with test compounds were incubated for 20 minutes at 37° C. To initiate the NE uptake, [$^3$H]NE diluted in assay buffer (120 nM final assay concentration) was delivered in 25 μl aliquots to each well and the plates were incubated for 5 minutes (37° C.). The reaction was terminated by decanting the supernatant from the plate. The plates containing cells were washed twice with 200 μl assay buffer (37° C.) to remove free radioligand. The plates were then inverted, left to dry for 2 minutes, then reinverted and air-dried for an additional 10 minutes. The cells were lysed in 25 μl of 0.25 N NaOH solution (4° C.), placed on a shake table and vigorously shaken for 5 minutes. After cell lysis, 75 μl of scintillation cocktail was added to each well and the plates were sealed with film tape. The plates were returned to the shake table and vigorously shaken for a minimum of 10 minutes to ensure adequate partitioning of organic and aqueous solutions. The plates were counted in a Wallac Microbeta counter (PerkinElmer) to collect the raw cpm data.

Serotonin (5-HT) Uptake Assay

The methods for 5-HT functional reuptake using the JAR cell line were modified using a previous literature report (Prasad, et al., *Placenta*, 1996. 17(4): 201-7). On day 1, cells were plated at 15,000 cells/well in 96-well plates containing growth medium (RPMI 1640 with 10% FBS) and maintained in a cell incubator (37° C., 5% $CO_2$). On day 2, cells were stimulated with staurosporine (40 nM) to increase the expression of the 5-HT transporter [17]. On day 3, cells were removed from the cell incubator two hours prior to assay and maintained at room temperature to equilibrate the growth medium to ambient oxygen concentration. Subsequently, the growth medium was replaced with 200 μl of assay buffer (25 mM HEPES; 120 mM NaCl; 5 mM KCl; 2.5 mM $CaCl_2$; 1.2 mM $MgSO_4$; 2 mg/ml glucose (pH 7.4, 37° C.)) containing 0.2 mg/ml ascorbic acid and 10 μM pargyline. A stock solution of paroxetine (AHR-4389-1) was prepared in DMSO (10 mM) and delivered to triplicate wells containing cells for a final test concentration of 1 μM. Data from these wells were used to define non-specific 5-HT uptake (minimum 5-HT uptake). Test compounds were prepared in DMSO (10 mM) and diluted in assay buffer according to test range (1 to 1,000 nM). Twenty-five microliters of assay buffer (maximum 5-HT uptake) or test compound were added directly to triplicate wells containing cells in 200 μl of assay buffer. The cells were incubated with the compound for 10 minutes (37° C.). To initiate the reaction, [$^3$H]hydroxytryptamine creatinine sulfate diluted in assay buffer was delivered in 25 μl aliquots to each well for a final test concentration of 15 nM. The cells were incubated with the reaction mixture for 5 minutes at 37° C. The 5-HT uptake reaction was terminated by decanting the assay buffer. The cells were washed twice with 200 μl assay buffer (37° C.) to remove free radioligand. The plates were inverted and left to dry for 2 minutes, then reinverted and air-dried for an additional 10 minutes. Subsequently, the cells were lysed in 25 μl of 0.25 N NaOH (4° C.) then placed on a shaker table and shaken vigorously for 5 minutes. After cell lysis, 75 μl of scintillation cocktail was added to the wells, the plates were sealed with film tape and replaced on the shake table for a minimum of 10 minutes. The plates were counted in a Wallac Microbeta counter (PerkinElmer) to collect the raw cpm data.

Evaluation of Results

For each experiment, a data stream of cpm values collected from the Wallac Microbeta counter was downloaded to a Microsoft Excel statistical application program. Calculations of $EC_{50}$ values were made using the transformed-both-sides logistic dose response program written by Wyeth Biometrics Department. The statistical program uses mean cpm values from wells representing maximum binding or uptake (assay buffer) and mean cpm values from wells representing minimum binding or uptake ((1 μM desipramine (hNET) or 1 μM paroxetine (hSERT)). Estimation of the $EC_{50}$ value was completed on a log scale and the line was fit between the maximum and minimum binding or uptake values. All graphic data representation was generated by normalizing each data point to a mean percent based on the maximum and minimum binding or uptake values. The $EC_{50}$ values reported from multiple experiments were calculated by pooling the raw data from each experiment and analyzing the pooled data as one experiment. The results are reported in Table 1.

TABLE 1

| Example | % Inhibition @ 1 μM (hNET) |
|---|---|
| 1 | 78 |
| 2 | 92 |
| 3 | 45 |
| 4 | 86 |
| 5 | 64 |
| 6 | 92 |
| 7 | 71 |
| 8 | 95 |
| 9 | 56 |
| 10 | 88 |
| 11 | 95 |
| 12 | 97 |
| 13 | 85 |
| 14 | 98 |
| 15 | 92 |
| 16 | 97 |
| 17 | 78 |
| 18 | 80 |
| 19 | 100 |
| 20 | 89 |
| 21 | 79 |
| 22 | 94 |
| 23 | 99 |
| 24 | 92 |
| 25 | 97 |
| 26 | 75 |
| 27 | 90 |
| 28 | 71 |
| 29 | 95 |
| 30 | 56 |
| 31 | 88 |
| 32 | 95 |

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula I:

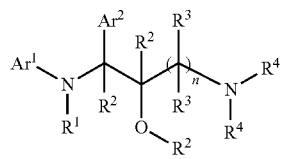

or a pharmaceutically acceptable salt thereof;
wherein:
n is 1 or 2;
$Ar^1$ is phenyl or naphthyl, wherein said phenyl or naphthyl is optionally substituted with up to 4 groups $R^5$;
$Ar^2$ is phenyl or naphthyl, wherein said phenyl or naphthyl is optionally substituted with up to 4 groups $R^5$;
$R^1$ is hydrogen or $C_1$-$C_3$ alkyl;
each $R^2$ is, independently, hydrogen or $C_1$-$C_3$ alkyl;
each $R^3$ is, independently, hydrogen or $C_1$-$C_3$ alkyl;
each $R^4$ is, independently, hydrogen or $C_1$-$C_4$ alkyl;
each $R^5$ is, independently, $C_1$-$C_3$ alkyl, $C_1$-$C_3$ alkoxy, halo, $CF_3$, $OCF_3$, hydroxy, nitro, nitrile, $C_2$-$C_4$ alkenyl, or $C_2$-$C_5$ alkynyl;
provided that said compound of formula I is other than 1-[(2-methoxyphenyl)(methyl)amino]-3-(methylamino)-1-phenylpropan-2-ol.

2. A compound according to claim 1,
wherein:
n is 1.

3. A compound according to claim 1,
wherein:
$Ar^1$ is an unsubstituted phenyl or an unsubstituted naphthyl.

4. A compound according to claim 1,
wherein:
$Ar^1$ is phenyl substituted with one $R^5$.

5. A compound according to claim 1,
wherein:
$Ar^1$ is an unsubstituted phenyl or an unsubstituted naphthyl.

6. A compound according to claim 1,
wherein:
$Ar^2$ is phenyl substituted with one $R^5$.

7. A compound according to claim 1,
wherein:
each group $R^5$ is, independently, methyl, methoxy, chloro, fluoro, $CF_3$, $OCF_3$, hydroxy, nitro, or nitrile.

8. A compound according to claim 1,
wherein:
each group $R^5$ is, independently, methyl, methoxy, chloro, or fluoro.

9. A compound according to claim 1,
wherein:
$R^1$ is hydrogen or methyl.

10. A compound according to claim 1,
wherein:
$R^1$ is methyl.

11. A compound according to claim 1,
wherein:
each $R^2$ is hydrogen.

12. A compound according to claim 1,
wherein:
each $R^3$ is hydrogen.

13. A compound according to claim 1,
wherein:
each $R^4$ is independently hydrogen, methyl, or ethyl.

14. A compound according to claim 1,
wherein:
at least one $R^4$ is hydrogen.

15. A compound according to claim 1,
wherein:
each $R^4$ is hydrogen.

16. A compound according to claim 1 selected from the group consisting of:
3-amino-1-[methyl(phenyl)amino]-1-phenylpropan-2-ol;
3-amino-1-[methyl(3-methylphenyl)amino]-1-phenylpropan-2-ol;
3-amino-1-[(2-chlorophenyl)(methyl)amino]-1-phenylpropan-2-ol;
3-amino-1-[(3-methoxyphenyl)(methyl)amino]-1-phenylpropan-2-ol;
3-amino-1-(4-methoxyphenyl)-1-[methyl(phenyl)amino]propan-2-ol;
3-amino-1-[(4-chlorophenyl)(methyl)amino]-1-(4-methoxyphenyl)propan-2-ol;
3-amino-1-(3-fluorophenyl)-1-[methyl(phenyl)amino]propan-2-ol;
3-(methylamino)-1-[methyl(phenyl)amino]-1-phenylpropan-2-ol;
3-(methylamino)-1-[methyl(phenyl)amino]-1-phenylpropan-2-ol;
3-(methylamino)-1-[methyl(2-methylphenyl)amino]-1-phenylpropan-2-ol;
3-(methylamino)-1-[methyl(3-methylphenyl)amino]-1-phenylpropan-2-ol;
3-(methylamino)-1-[methyl(4-methylphenyl)amino]-1-phenylpropan-2-ol;
1-[(2-chlorophenyl)(methyl)amino]-3-(methylamino)-1-phenylpropan-2-ol;
1-[(3-chlorophenyl)(methyl)amino]-3-(methylamino)-1-phenylpropan-2-ol;
1-[(4-fluorophenyl)(methyl)amino]-3-(methylamino)-1-phenylpropan-2-ol;
1-[(4-chlorophenyl)(methyl)amino]-3-(methylamino)-1-phenylpropan-2-ol;
1-[(3-methoxyphenyl)(methyl)amino]-3-(methylamino)-1-phenylpropan-2-ol;
1-[(4-methoxyphenyl)(methyl)amino]-3-(methylamino)-1-phenylpropan-2-ol;
1-(3-fluorophenyl)-3-(methylamino)-1-[methyl(phenyl)amino]propan-2-ol;
1-(3-chlorophenyl)-3-(methylamino)-1-[methyl(phenyl)amino]propan-2-ol;
1-(4-chlorophenyl)-3-(methylamino)-1-[methyl(phenyl)amino]propan-2-ol;
1-(4-methoxyphenyl)-3-(methylamino)-1-[methyl(phenyl)amino]propan-2-ol;
1-[(4-chlorophenyl)(methyl)amino]-1-(3-fluorophenyl)-3-(methylamino)propan-2-ol;
1-[(3-fluorophenyl)(methyl)amino]-1-(4-methoxyphenyl)-3-(methylamino)propan-2-ol;
1-[(4-chlorophenyl)(methyl)amino]-1-(4-methoxyphenyl)-3-(methylamino)propan-2-ol;
1-(4-methoxyphenyl)-1-[(4-methoxyphenyl)(methyl)amino]-3-(methylamino)propan-2-ol;
3-(methylamino)-1-[methyl(1-naphthyl)amino]-1-phenylpropan-2-ol;

3-(ethylamino)-1-[methyl(4-methylphenyl)amino]-1-phenylpropan-2-ol;
1-[(4-chlorophenyl)(methyl)amino]-3-(ethylamino)-1-(4-methoxyphenyl)propan-2-ol;
1-(3-chlorophenyl)-3-(ethylamino)-1-[methyl(phenyl)amino]propan-2-ol;
1-(4-chlorophenyl)-3-(ethylamino)-1-[methyl(phenyl)amino]propan-2-ol; and
3-(dimethylamino)-1-[methyl(4-methylphenyl)amino]-1-phenylpropan-2-ol;
stereoisomers and pharmaceutically acceptable salts thereof.

17. A compound according to claim 1 selected from the group consisting of:
(1RS,2SR)-3-amino-1-[methyl(phenyl)amino]-1-phenylpropan-2-ol;
(1RS,2SR)-3-amino-1-[methyl (3-methylphenyl)amino]-1-phenylpropan-2-ol;
(1RS,2SR)-3-amino-1-[(2-chlorophenyl)(methyl)amino]-1-phenylpropan-2-ol;
(1RS,2SR)-3-amino-1-[(3-methoxyphenyl)(methyl)amino]-1-phenylpropan-2-ol;
(1RS,2SR)-3-amino-1-(4-methoxyphenyl)-1-[methyl(phenyl)amino]propan-2-ol;
(1RS,2SR)-3-amino-1-[(4-chlorophenyl)(methyl)amino]-1-(4-methoxyphenyl)propan-2-ol;
(1RS,2SR)-3-amino-1-(3-fluorophenyl)-1-[methyl(phenyl)amino]propan-2-ol;
(1RS,2SR)-3-(methylamino)-1-[methyl(phenyl)amino]-1-phenylpropan-2-ol;
(1RS,2RS)-3-(methylamino)-1-[methyl(phenyl)amino]-1-phenylpropan-2-ol;
(1RS,2SR)-3-(methylamino)-1-[methyl(2-methylphenyl)amino]-1-phenylpropan-2-ol;
(1RS,2SR)-3-(methylamino)-1-[methyl(3-methylphenyl)amino]-1-phenylpropan-2-ol;
(1RS,2SR)-3-(methylamino)-1-[methyl(4-methylphenyl)amino]-1-phenylpropan-2-ol;
(1RS,2SR)-1-[(2-chlorophenyl)(methyl)amino]-3-(methylamino)-1-phenylpropan-2-ol;
(1RS,2SR)-1-[(3-chlorophenyl)(methyl)amino]-3-(methylamino)-1-phenylpropan-2-ol;
(1RS,2SR)-1-[(4-fluorophenyl)(methyl)amino]-3-(methylamino)-1-phenylpropan-2-ol;
(1RS,2SR)-1-[(4-chlorophenyl)(methyl)amino]-3-(methylamino)-1-phenylpropan-2-ol;
(1RS,2SR)-1-[(3-methoxyphenyl)(methyl)amino]-3-(methylamino)-1-phenylpropan-2-ol;
(1RS,2SR)-1-[(4-methoxyphenyl)(methyl)amino]-3-(methylamino)-1-phenylpropan-2-ol;
(1RS,2SR)-1-(3-fluorophenyl)-3-(methylamino)-1-[methyl(phenyl)amino]propan-2-ol;
(1RS,2SR)-1-(3-chlorophenyl)-3-(methylamino)-1-[methyl(phenyl)amino]propan-2-ol;
(1RS,2SR)-1-(4-chlorophenyl)-3-(methylamino)-1-[methyl(phenyl)amino]propan-2-ol;
(1RS,2SR)-1-(4-methoxyphenyl)-3-(methylamino)-1-[methyl(phenyl)amino]propan-2-ol;
(1RS,2SR)-1-[(4-chlorophenyl)(methyl)amino]-1-(3-fluorophenyl)-3-(methylamino)propan-2-ol;
(1RS,2SR)-1-[(3-fluorophenyl)(methyl)amino]-1-(4-methoxyphenyl)-3-(methylamino)propan-2-ol;
(1RS,2SR)-1-[(4-chlorophenyl)(methyl)amino]-1-(4-methoxyphenyl)-3-(methylamino)propan-2-ol;
(1RS,2SR)-1-(4-methoxyphenyl)-1-[(4-methoxyphenyl)(methyl)amino]-3-(methylamino)propan-2-ol;
(1RS,2SR)-3-(methylamino)-1-[methyl(1-naphthyl)amino]-1-phenylpropan-2-ol;
(1RS,2SR)-3-(ethylamino)-1-[methyl (4-methylphenyl)amino]-1-phenylpropan-2-ol;
(1RS,2SR)-1-[(4-chlorophenyl)(methyl)amino]-3-(ethylamino)-1-(4-methoxyphenyl)propan-2-ol;
(1RS,2SR)-1-(3-chlorophenyl)-3-(ethylamino)-1-[methyl(phenyl)amino]propan-2-ol;
(1RS,2SR)-1-(4-chlorophenyl)-3-(ethylamino)-1-[methyl(phenyl)amino]propan-2-ol;
(1RS,2SR)-3-(dimethylamino)-1-[methyl(4-methylphenyl)amino]-1-phenylpropan-2-ol; and
pharmaceutically acceptable salts thereof.

18. A compound according to claim 1,
wherein said pharmaceutically acceptable salt is a hydrochloride.

19. A composition, comprising:
a. at least one compound according to claim 1; and
b. at least one pharmaceutically acceptable carrier.

* * * * *